(12) United States Patent
Spencer et al.

(10) Patent No.: US 7,659,445 B2
(45) Date of Patent: Feb. 9, 2010

(54) EXPRESSION OF PLASMINOGEN AND MICROPLASMINOGEN IN DUCK WEED

(75) Inventors: David Spencer, Chapel Hill, NC (US);
Lynn F. Dickey, Cary, NC (US); John R. Gasdaska, Carrboro, NC (US);
Xiaowei Wang, Carrboro, NC (US);
Kevin M. Cox, Raleigh, NC (US);
Charles G. Peele, Apex, NC (US)

(73) Assignee: Biolex Therapeutics, Inc., Pittsboro, NC (US)

( * ) Notice: Subject to any disclaimer, the term of this patent is extended or adjusted under 35 U.S.C. 154(b) by 0 days.

(21) Appl. No.: 11/056,621

(22) Filed: Feb. 11, 2005

(65) Prior Publication Data

US 2005/0262592 A1 Nov. 24, 2005

Related U.S. Application Data

(60) Provisional application No. 60/543,487, filed on Feb. 11, 2004.

(51) Int. Cl.
*C12N 15/82* (2006.01)
*C12N 15/12* (2006.01)
*C12N 15/62* (2006.01)

(52) U.S. Cl. ............... 800/288; 435/69.6; 435/69.8; 536/24.1

(58) Field of Classification Search .................. None
See application file for complete search history.

(56) References Cited

U.S. PATENT DOCUMENTS

| 5,648,254 | A | 7/1997 | Mulvihill et al. | |
|---|---|---|---|---|
| 6,815,184 | B2 * | 11/2004 | Stomp et al. | 435/69.51 |
| 2003/0115640 | A1 | 6/2003 | Stomp et al. | |
| 2006/0195946 | A1 * | 8/2006 | Dickey et al. | 800/288 |

FOREIGN PATENT DOCUMENTS

| WO | WO 02/10414 | A2 | | 2/2002 |
|---|---|---|---|---|
| WO | WO 02/50290 | A1 | | 6/2002 |
| WO | WO 02/10414 | | * | 7/2002 |
| WO | WO 2005/005643 | A2 | | 1/2005 |
| WO | WO 2005/005643 | A3 | | 1/2005 |
| WO | WO 2005/105990 | A2 | | 11/2005 |

OTHER PUBLICATIONS

Kim, et al, A_Geneseq_21 Database. Accession No. ABB83470, WO 200253191-A1, Jul. 11, 2002.*
Buzby, et al, GenEMBL Database. Accession No. S45167, Plant Cell 2(8), 804-14 (1990).*
Stomp, et al, GenEMBL Database. Accession No. AX393895, WO 200210414-A1, Feb. 7, 2002.*
Silverthorne et al. Plant Molecular Biology 15(1): 49-58 (1990).*
Whitefleet-Smith et al. Archives of Biochemistry and Biophysics 271(2): 390-399 (Jun. 1989).*
Nilsen et al. Protein Expression and Purification 19: 136-143 (1999).*
Leytus et al. Proc. Natl. Acad. Sci. USA 78(3): 1485-1489 (Mar. 1981).*
Managing Intellectual Property, Jul./Aug. 2008, pp. 28, 50 and 51.*
Gasdaska, J., et al., "Advantages of Therapeutic Protein Production in the Aquatic Plant *Lemna*," *Bioprocessing: Advances and Trends in Biological Product Development*, 2003, pp. 49-56, vol. 2.
Turner, R., et al., "Structural Elements That Govern the Substrate Specificity of the Clot-dissolving Enzyme Plasmin," *The Journal of Biological Chemistry*, 2002, pp. 33068-33074, vol. 277 (36).
Yamamoto, Y., et al., "Genetic Transformation of Duckweed *Lemna gibba* and *Lemna minor*," In Vitro *Cellular & Development Biology-Plant*, 2001, pp. 349-353, vol. 37 (3).

* cited by examiner

*Primary Examiner*—David T Fox
(74) *Attorney, Agent, or Firm*—Alston & Bird LLP

(57) ABSTRACT

The present invention provides methods and compositions for the production of recombinant plasminogen, microplasminogen, and fragments thereof in a duckweed expression system. It is the novel finding of the present invention that a duckweed expression system may be used to produce high levels of plasminogen and microplasminogen. The duckweed-produced plasminogen and microplasminogen can be activated to produce a polypeptide having protease activity. Thus, the invention encompasses methods for the expression of plasminogen, microplasminogen, and fragments thereof in duckweed, duckweed plants that are transformed with expression cassettes for the expression of plasminogen, microplasminogen, and fragments thereof, and nucleic acids comprising nucleotide sequences encoding plasminogen, microplasminogen, and fragments thereof, where these nucleotide sequences are modified to enhance their expression in duckweed.

16 Claims, 8 Drawing Sheets

```
                          SEQUENCE LISTING

<160> NUMBER OF SEQ ID NOS: 9

<210> SEQ ID NO 1
<211> LENGTH: 554
<212> TYPE: DNA
<213> ORGANISM: Zea mays

<400> SEQUENCE: 1
gatcaagtgc aaaggtccgc cttgtttctc ctctgtctct tgatctgact aatcttggtt      60
tatgattcgt tgagtaattt tggggaaagc ttcgtccaca gttttttttt cgatgaacag     120
tgccgcagtg gcgctgatct tgtatgctat cctgcaatcg tggtgaactt atgtctttta     180
tatccttcac taccatgaaa agactagtaa tctttctcga tgtaacatcg tccagcactg     240
ctattaccgt gtggtccatc cgacagtctg gctgaacaca tcatacgata ttgagcaaag     300
atctatcttc cctgttcttt aatgaaagac gtcattttca tcagtatgat ctaagaatgt     360
tgcaacttgc aaggaggcgt ttctttcttt gaatttaact aactcgttga gtggccctgt     420
ttctcggacg taaggccttt gctgctccac acatgtccat tcgaattta ccgtgtttag      480 caagggcgaa aagtttgcat cttgatgatt tagcttgact atgcgattgc tttcctggac     540
ccgtgcagct gcgg                                                      554

<210> SEQ ID NO 2
<211> LENGTH: 63
<212> TYPE: DNA
<213> ORGANISM: Lemna gibba

<400> SEQUENCE: 2
gaaactcccg aggtgagcaa ggatccggag tcgagcgcga agaagagaaa gagggaaagc      60
gcg                                                                   63

<210> SEQ ID NO 3
<211> LENGTH: 2376
```

<210> TYPE: DNA
<213> ORGANISM: Artificial Sequence
<220> FEATURE:
<223> OTHER INFORMATION: Duckweed codon optimized sequence encoding human plasminogen
<220> FEATURE:
<221> NAME/KEY: CDS
<222> LOCATION: (1)...(2376)

<400> SEQUENCE: 3

```
gag ccc ctg gac gac tac gtg aac acg cag ggc gcc tcc ctg ttc agc        48
Glu Pro Leu Asp Asp Tyr Val Asn Thr G -continued

| | |
|---|---|
| tcc ggg cac acc tgc caa cac tgg agc gcg cag acc ccg cac acc cac<br>Ser Gly His Thr Cys Gln His Trp Ser Ala Gln Thr Pro His Thr His<br>275                     280                     285 | 864 |
| aac cgg acg ccg gag aac ttc ccc tgc aag aac ctg gac gag aac tac<br>Asn Arg Thr Pro Glu Asn Phe Pro Cys Lys Asn Leu Asp Glu Asn Tyr<br>290                     295                     300 | 912 |
| tgc cgc aac ccg gac ggg aag cgt gcc ccg tgg tgc cac acc acc aac<br>Cys Arg Asn Pro Asp Gly Lys Arg Ala Pro Trp Cys His Thr Thr Asn<br>305                     310                     315                     320 | 960 |
| agc cag gtt cgc tgg gag tac tgc aag atc ccg tcc tgc gat tcc tct<br>Ser Gln Val Arg Trp Glu Tyr Cys Lys Ile Pro Ser Cys Asp Ser Ser<br>                     325                     330                     335 | 1008 |
| ccg gtc tcc act gag cag ctg gcg ccc acc gcg ccg ccc gaa ctc acg<br>Pro Val Ser Thr Glu Gln Leu Ala Pro Thr Ala Pro Pro Glu Leu Thr<br>                     340                     345                     350 | 1056 |
| ccg gtg gtc cag gac tgc tat cac ggc gac ggg cag agc tac cgc ggc<br>Pro Val Val Gln Asp Cys Tyr His Gly Asp Gly Gln Ser Tyr Arg Gly<br>                     355                     360                     365 | 1104 |
| acc tct tcc acc act acc acg ggc aag aag tgc cag tcc tgg tcc agc<br>Thr Ser Ser Thr Thr Thr Thr Gly Lys Lys Cys Gln Ser Trp Ser Ser<br>370                     375                     380 | 1152 |
| atg acc cct cac cgg cac cag aag acc ccg gag aac tac ccg aac gcc<br>Met Thr Pro His Arg His Gln Lys Thr Pro Glu Asn Tyr Pro Asn Ala<br>385                     390                     395                     400 | 1200 |
| ggc ctg acc atg aac tac tgc agg aac ccg gac gcc gac aaa ggc ccc<br>Gly Leu Thr Met Asn Tyr Cys Arg Asn Pro Asp Ala Asp Lys Gly Pro<br>                                 405                     410                     415 | 1248 |
| tgg tgc ttc acc acc gat ccc agc gtc cgc tgg gag tac tgc aac ctg<br>Trp Cys Phe Thr Thr Asp Pro Ser Val Arg Trp Glu Tyr Cys Asn Leu<br>                     420                     425                     430 | 1296 |
| aag aaa tgc tcc ggc acc gag gcg agc gtc gtc gcg ccg cca ccc gtg<br>Lys Lys Cys Ser Gly Thr Glu Ala Ser Val Val Ala Pro Pro Pro Val<br>                     435                     440                     445 | 1344 |
| gtc ctg ctt ccg gac gtc gag acc ccg tcc gag gag gac tgc atg ttc<br>Val Leu Leu Pro Asp Val Glu Thr Pro Ser Glu Glu Asp Cys Met Phe<br>450                     455                     460 | 1392 |
| ggg aac ggg aag ggc tac cgc ggc aag cgc gcg acc act gtc acc ggg<br>Gly Asn Gly Lys Gly Tyr Arg Gly Lys Arg Ala Thr Thr Val Thr Gly<br>465                     470                     475                     480 | 1440 |
| acc ccg tgc cag gac tgg gcc gct cag gag ccc cac agg cac agc atc<br>Thr Pro Cys Gln Asp Trp Ala Ala Gln Glu Pro His Arg His Ser Ile<br>                                 485                     490                     495 | 1488 |
| ttc acc ccg gag acc aac ccg cgc gcg ggc ctg gag aag aac tac tgc<br>Phe Thr Pro Glu Thr Asn Pro Arg Ala Gly Leu Glu Lys Asn Tyr Cys<br>                     500                     505                     510 | 1536 |
| cgc aac ccg gac ggc gac gtt gga ggc ccc tgg tgc tac act acc aac<br>Arg Asn Pro Asp Gly Asp Val Gly Gly Pro Trp Cys Tyr Thr Thr Asn<br>                     515                     520                     525 | 1584 |
| ccg cgt aag ctc tac gac tac tgc gac gtc ccg cag tgc gcg gct ccg<br>Pro Arg Lys Leu Tyr Asp Tyr Cys Asp Val Pro Gln Cys Ala Ala Pro<br>530                     535                     540 | 1632 |
| tcc ttc gac tgc ggg aag cca cag gtg gaa ccg aag aag tgc cct ggc<br>Ser Phe Asp Cys Gly Lys Pro Gln Val Glu Pro Lys Lys Cys Pro Gly<br>545                     550                     555                     560 | 1680 |
| cgc gtg gtc gga ggg tgc gtg gcc cac ccg cac tcc tgg ccc tgg caa<br>Arg Val Val Gly Gly Cys Val Ala His Pro His Ser Trp Pro Trp Gln<br>                     565                     570                     575 | 1728 |
| gtc agc ctg cgc acc cgc ttc ggc atg cac ttc tgc ggc ggc acc ctc<br>Val Ser Leu Arg Thr Arg Phe Gly Met His Phe Cys Gly Gly Thr Leu<br>                     580                     585                     590 | 1776 |

```
atc tcc ccg gag tgg gtt ctg acc gcc gct cac tgc ctc gag aag tcc      1824
Ile Ser Pro Glu Trp Val Leu Thr Ala Ala His Cys Leu Glu Lys Ser
        595                 600                 605 ccg agg ccc tcc tcc tac aag gtc atc ctg ggc gcc cac cag gag gtg      1872
Pro Arg Pro Ser Ser Tyr Lys Val Ile Leu Gly Ala His Gln Glu Val
    610                 615                 620 aac ctc gag ccg cac gtt cag gag atc gag gtg tcc cgc ttg ttc ctg      1920
Asn Leu Glu Pro His Val Gln Glu Ile Glu Val Ser Arg Leu Phe Leu
625                 630                 635                 640 gag ccc acg cgc aag gat atc gcc ctg ctc aag ctc tct agc ccg gcc      1968
Glu Pro Thr Arg Lys Asp Ile Ala Leu Leu Lys Leu Ser Ser Pro Ala
                645                 650                 655 gtc atc acc gac aag gtt atc ccg gcc tgc ctt ccc tcc ccg aac tac      2016
Val Ile Thr Asp Lys Val Ile Pro Ala Cys Leu Pro Ser Pro Asn Tyr
            660                 665                 670 gtg gtc gct gac cgc acc gag tgc ttc gtt acc ggc tgg ggc gag acc      2064
Val Val Ala Asp Arg Thr Glu Cys Phe Val Thr Gly Trp Gly Glu Thr
        675                 680                 685 cag gga acg ttc ggc gcg ggc ctc ctc aag gag gcc cag ctc ccg gtg      2112
Gln Gly Thr Phe Gly Ala Gly Leu Leu Lys Glu Ala Gln Leu Pro Val
    690                 695                 700 att gag aac aag gtg tgc aac cgt tac gag ttc ctg aac ggg cgc gtc      2160
Ile Glu Asn Lys Val Cys Asn Arg Tyr Glu Phe Leu Asn Gly Arg Val
705                 710                 715                 720 cag tcc acc gaa ctc tgc gcc ggg cac ttg gcc ggc ggc acc gac agc      2208
Gln Ser Thr Glu Leu Cys Ala Gly His Leu Ala Gly Gly Thr Asp Ser
                725                 730                 735 tgc cag ggc gac agc ggc ggg ccg ctg gtg tgc ttc gag aag gac aag      2256
Cys Gln Gly Asp Ser Gly Gly Pro Leu Val Cys Phe Glu Lys Asp Lys
            740                 745                 750 tac atc ctc caa ggc gtc acg tcc tgg ggc ctc ggc tgc gca cgc cct      2304
Tyr Ile Leu Gln Gly Val Thr Ser Trp Gly Leu Gly Cys Ala Arg Pro
        755                 760                 765 aac aag ccg ggc gtc tat gtg cgc gtg tcc cgc ttc gtg acc tgg atc      2352
Asn Lys Pro Gly Val Tyr Val Arg Val Ser Arg Phe Val Thr Trp Ile
    770                 775                 780 gag ggc gtg atg cgc aac aac taa                                      2376
Glu Gly Val Met Arg Asn Asn *
785                 790

<210> SEQ ID NO 4
<211> LENGTH: 791
<212> TYPE: PRT
<213> ORGANISM: Artificial Sequence
<220> FEATURE:
<223> OTHER INFORMATION: Sequence of mature human plasminogen

<400> SEQUENCE: 4

Glu Pro Leu Asp Asp Tyr Val Asn Thr Gln Gly Ala Ser Leu Phe Ser
1               5                   10                  15

Val Thr Lys Lys Gln Leu Gly Ala Gly Ser Ile Glu Glu Cys Ala Ala
            20                  25                  30

Lys Cys Glu Glu Asp Glu Glu Phe Thr Cys Arg Ala Phe Gln Tyr His
        35                  40                  45

Ser Lys Glu Gln Gln Cys Val Ile Met Ala Glu Asn Arg Lys Ser Ser
    50                  55                  60

Ile Ile Ile Arg Met Arg Asp Val Val Leu Phe Glu Lys Lys Val Tyr
65                  70                  75                  80

Leu Ser Glu Cys Lys Thr Gly Asn Gly Lys Asn Tyr Arg Gly Thr Met
```

-continued

```
                    85                  90                  95
Ser Lys Thr Lys Asn Gly Ile Thr Cys Gln Lys Trp Ser Ser Thr Ser
                100                 105                 110
Pro His Arg Pro Arg Phe Ser Pro Ala Thr His Pro Ser Glu Gly Leu
                115                 120                 125
Glu Glu Asn Tyr Cys Arg Asn Pro Asp Asn Asp Pro Gln Gly Pro Trp
            130                 135                 140
Cys Tyr Thr Thr Asp Pro Glu Lys Arg Tyr Asp Tyr Cys Asp Ile Leu
145                 150                 155                 160
Glu Cys Glu Glu Glu Cys Met His Cys Ser Gly Glu Asn Tyr Asp Gly
                165                 170                 175
Lys Ile Ser Lys Thr Met Ser Gly Leu Glu Cys Gln Ala Trp Asp Ser
                180                 185                 190
Gln Ser Pro His Ala His Gly Tyr Ile Pro Ser Lys Phe Pro Asn Lys
                195                 200                 205
Asn Leu Lys Lys Asn Tyr Cys Arg Asn Pro Asp Arg Glu Leu Arg Pro
            210                 215                 220
Trp Cys Phe Thr Thr Asp Pro Asn Lys Arg Trp Glu Leu Cys Asp Ile
225                 230                 235                 240
Pro Arg Cys Thr Thr Pro Pro Ser Ser Gly Pro Thr Tyr Gln Cys
                245                 250                 255
Leu Lys Gly Thr Gly Glu Asn Tyr Arg Gly Asn Val Ala Val Thr Val
                260                 265                 270
Ser Gly His Thr Cys Gln His Trp Ser Ala Gln Thr Pro His Thr His
                275                 280                 285
Asn Arg Thr Pro Glu Asn Phe Pro Cys Lys Asn Leu Asp Glu Asn Tyr
            290                 295                 300
Cys Arg Asn Pro Asp Gly Lys Arg Ala Pro Trp Cys His Thr Thr Asn
305                 310                 315                 320
Ser Gln Val Arg Trp Glu Tyr Cys Lys Ile Pro Ser Cys Asp Ser Ser
                325                 330                 335
Pro Val Ser Thr Glu Gln Leu Ala Pro Thr Ala Pro Pro Glu Leu Thr
                340                 345                 350
Pro Val Val Gln Asp Cys Tyr His Gly Asp Gly Gln Ser Tyr Arg Gly
                355                 360                 365
Thr Ser Ser Thr Thr Thr Thr Gly Lys Lys Cys Gln Ser Trp Ser Ser
            370                 375                 380
Met Thr Pro His Arg His Gln Lys Thr Pro Glu Asn Tyr Pro Asn Ala
385                 390                 395                 400
Gly Leu Thr Met Asn Tyr Cys Arg Asn Pro Asp Ala Asp Lys Gly Pro
                405                 410                 415
Trp Cys Phe Thr Thr Asp Pro Ser Val Arg Trp Glu Tyr Cys Asn Leu
                420                 425                 430
Lys Lys Cys Ser Gly Thr Glu Ala Ser Val Val Ala Pro Pro Val
            435                 440                 445
Val Leu Leu Pro Asp Val Glu Thr Pro Ser Glu Glu Asp Cys Met Phe
            450                 455                 460
Gly Asn Gly Lys Gly Tyr Arg Gly Lys Arg Ala Thr Thr Val Thr Gly
465                 470                 475                 480
Thr Pro Cys Gln Asp Trp Ala Ala Gln Glu Pro His Arg His Ser Ile
                485                 490                 495
Phe Thr Pro Glu Thr Asn Pro Arg Ala Gly Leu Glu Lys Asn Tyr Cys
                500                 505                 510
```

```
Arg Asn Pro Asp Gly Asp Val Gly Gly Pro Trp Cys Tyr Thr Thr Asn
        515                 520                 525
Pro Arg Lys Leu Tyr Asp Tyr Cys Asp Val Pro Gln Cys Ala Ala Pro
        530                 535                 540
Ser Phe Asp Cys Gly Lys Pro Gln Val Glu Pro Lys Lys Cys Pro Gly
545                 550                 555                 560
Arg Val Val Gly Gly Cys Val Ala His Pro His Ser Trp Pro Trp Gln
                565                 570                 575
Val Ser Leu Arg Thr Arg Phe Gly Met His Phe Cys Gly Gly Thr Leu
            580                 585                 590
Ile Ser Pro Glu Trp Val Leu Thr Ala Ala His Cys Leu Glu Lys Ser
        595                 600                 605
Pro Arg Pro Ser Ser Tyr Lys Val Ile Leu Gly Ala His Gln Glu Val
        610                 615                 620
Asn Leu Glu Pro His Val Gln Glu Ile Glu Val Ser Arg Leu Phe Leu
625                 630                 635                 640
Glu Pro Thr Arg Lys Asp Ile Ala Leu Leu Lys Leu Ser Ser Pro Ala
                645                 650                 655
Val Ile Thr Asp Lys Val Ile Pro Ala Cys Leu Pro Ser Pro Asn Tyr
            660                 665                 670
Val Val Ala Asp Arg Thr Glu Cys Phe Val Thr Gly Trp Gly Glu Thr
        675                 680                 685
Gln Gly Thr Phe Gly Ala Gly Leu Leu Lys Glu Ala Gln Leu Pro Val
        690                 695                 700
Ile Glu Asn Lys Val Cys Asn Arg Tyr Glu Phe Leu Asn Gly Arg Val
705                 710                 715                 720
Gln Ser Thr Glu Leu Cys Ala Gly His Leu Ala Gly Gly Thr Asp Ser
                725                 730                 735
Cys Gln Gly Asp Ser Gly Gly Pro Leu Val Cys Phe Glu Lys Asp Lys
            740                 745                 750
Tyr Ile Leu Gln Gly Val Thr Ser Trp Gly Leu Gly Cys Ala Arg Pro
        755                 760                 765
Asn Lys Pro Gly Val Tyr Val Arg Val Ser Arg Phe Val Thr Trp Ile
        770                 775                 780
Glu Gly Val Met Arg Asn Asn
785                 790

<210> SEQ ID NO 5
<211> LENGTH: 780
<212> TYPE: DNA
<213> ORGANISM: Artificial Sequence
<220> FEATURE:
<223> OTHER INFORMATION: Duckweed codon optimized sequence encoding
      human microplasminogen
<220> FEATURE:
<221> NAME/KEY: CDS
<222> LOCATION: (1)...(780)

<400> SEQUENCE: 5 gag ccc ctg gac gac tac gtg aac acg cag ggc ccg tcc ttc gac tgc      48
Glu Pro Leu Asp Asp Tyr Val Asn Thr Gln Gly Pro Ser Phe Asp Cys
 1               5                  10                  15 ggg aag cca cag gtg gaa ccg aag aag tgc cct ggc cgc gtg gtc gga      96
Gly Lys Pro Gln Val Glu Pro Lys Lys Cys Pro Gly Arg Val Val Gly
             20                  25                  30 ggg tgc gtg gcc cac ccg cac tcc tgg ccc tgg caa gtc agc ctg cgc     144
Gly Cys Val Ala His Pro His Ser Trp Pro Trp Gln Val Ser Leu Arg
```

```
                35                  40                  45
acc cgc ttc ggc atg cac ttc tgc ggc ggc acc ctc atc tcc ccg gag    192
Thr Arg Phe Gly Met His Phe Cys Gly Gly Thr Leu Ile Ser Pro Glu
    50                  55                  60 tgg gtt ctg acc gcc gct cac tgc ctc gag aag tcc ccg agg ccc tcc    240
Trp Val Leu Thr Ala Ala His Cys Leu Glu Lys Ser Pro Arg Pro Ser
65                  70                  75                  80 tcc tac aag gtc atc ctg ggc gcc cac cag gag gtg aac ctc gag ccg    288
Ser Tyr Lys Val Ile Leu Gly Ala His Gln Glu Val Asn Leu Glu Pro
                85                  90                  95 cac gtt cag gag atc gag gtg tcc cgc ttg ttc ctg gag ccc acg cgc    336
His Val Gln Glu Ile Glu Val Ser Arg Leu Phe Leu Glu Pro Thr Arg
            100                 105                 110 aag gat atc gcc ctg ctc aag ctc tct agc ccg gcc gtc atc acc gac    384
Lys Asp Ile Ala Leu Leu Lys Leu Ser Ser Pro Ala Val Ile Thr Asp
            115                 120                 125 aag gtt atc ccg gcc tgc ctt ccc tcc ccg aac tac gtg gtc gct gac    432
Lys Val Ile Pro Ala Cys Leu Pro Ser Pro Asn Tyr Val Val Ala Asp
    130                 135                 140 cgc acc gag tgc ttc gtt acc ggc tgg ggc gag acc cag gga acg ttc    480
Arg Thr Glu Cys Phe Val Thr Gly Trp Gly Glu Thr Gln Gly Thr Phe
145                 150                 155                 160 ggc gcg ggc ctc ctc aag gag gcc cag ctc ccg gtg att gag aac aag    528
Gly Ala Gly Leu Leu Lys Glu Ala Gln Leu Pro Val Ile Glu Asn Lys
                165                 170                 175 gtg tgc aac cgt tac gag ttc ctg aac ggg cgc gtc cag tcc acc gaa    576
Val Cys Asn Arg Tyr Glu Phe Leu Asn Gly Arg Val Gln Ser Thr Glu
            180                 185                 190 ctc tgc gcc ggg cac ttg gcc ggc ggc acc gac agc tgc cag ggc gac    624
Leu Cys Ala Gly His Leu Ala Gly Gly Thr Asp Ser Cys Gln Gly Asp
            195                 200                 205 agc ggg ggg ccg ctg gtg tgc ttc gag aag gac aag tac atc ctc caa    672
Ser Gly Gly Pro Leu Val Cys Phe Glu Lys Asp Lys Tyr Ile Leu Gln
    210                 215                 220 ggc gtc acg tcc tgg ggc ctc ggc tgc gca cgc cct aac aag ccg ggc    720
Gly Val Thr Ser Trp Gly Leu Gly Cys Ala Arg Pro Asn Lys Pro Gly
225                 230                 235                 240 gtc tat gtg cgc gtg tcc cgc ttc gtg acc tgg atc gag ggc gtg atg    768
Val Tyr Val Arg Val Ser Arg Phe Val Thr Trp Ile Glu Gly Val Met
                245                 250                 255 cgc aac aac taa                                                     780
Arg Asn Asn *
```

<210> SEQ ID NO 6
<211> LENGTH: 259
<212> TYPE: PRT
<213> ORGANISM: Artificial Sequence
<220> FEATURE:
<223> OTHER INFORMATION: Sequence of mature human microplasminogen

<400> SEQUENCE: 6

```
Glu Pro Leu Asp Asp Tyr Val Asn Thr Gln Gly Pro Ser Phe Asp Cys
1               5                   10                  15

Gly Lys Pro Gln Val Glu Pro Lys Lys Cys Pro Gly Arg Val Val Gly
            20                  25                  30

Gly Cys Val Ala His Pro His Ser Trp Pro Trp Gln Val Ser Leu Arg
        35                  40                  45

Thr Arg Phe Gly Met His Phe Cys Gly Gly Thr Leu Ile Ser Pro Glu
    50                  55                  60
```

```
Trp Val Leu Thr Ala Ala His Cys Leu Glu Lys Ser Pro Arg Pro Ser
 65                  70                  75                  80

Ser Tyr Lys Val Ile Leu Gly Ala His Gln Glu Val Asn Leu Glu Pro
                 85                  90                  95

His Val Gln Glu Ile Glu Val Ser Arg Leu Phe Leu Glu Pro Thr Arg
            100                 105                 110

Lys Asp Ile Ala Leu Leu Lys Leu Ser Ser Pro Ala Val Ile Thr Asp
        115                 120                 125

Lys Val Ile Pro Ala Cys Leu Pro Ser Pro Asn Tyr Val Val Ala Asp
    130                 135                 140

Arg Thr Glu Cys Phe Val Thr Gly Trp Gly Thr Gln Gly Thr Phe
145                 150                 155                 160

Gly Ala Gly Leu Leu Lys Glu Ala Gln Leu Pro Val Ile Glu Asn Lys
                165                 170                 175

Val Cys Asn Arg Tyr Glu Phe Leu Asn Gly Arg Val Gln Ser Thr Glu
            180                 185                 190

Leu Cys Ala Gly His Leu Ala Gly Gly Thr Asp Ser Cys Gln Gly Asp
        195                 200                 205

Ser Gly Gly Pro Leu Val Cys Phe Glu Lys Asp Lys Tyr Ile Leu Gln
    210                 215                 220

Gly Val Thr Ser Trp Gly Leu Gly Cys Ala Arg Pro Asn Lys Pro Gly
225                 230                 235                 240

Val Tyr Val Arg Val Ser Arg Phe Val Thr Trp Ile Glu Gly Val Met
                245                 250                 255

Arg Asn Asn

<210> SEQ ID NO 7
<211> LENGTH: 96
<212> TYPE: DNA
<213> ORGANISM: Oryza sativa
<220> FEATURE:
<221> NAME/KEY: CDS
<222> LOCATION: (4)...(96)

<400> SEQUENCE: 7 acc atg cag gtc ctg aac acg atg gtc aac aag cac ttc ctc tcc ctg      48
    Met Gln Val Leu Asn Thr Met Val Asn Lys His Phe Leu Ser Leu
     1               5                  10                  15 tcc gtc ctc atc gtc ctc ctc ggg ctg agc agc aac ctc acc gcc ggc      96
Ser Val Leu Ile Val Leu Leu Gly Leu Ser Ser Asn Leu Thr Ala Gly
                20                  25                  30

<210> SEQ ID NO 8
<211> LENGTH: 31
<212> TYPE: PRT
<213> ORGANISM: Oryza sativa

<400> SEQUENCE: 8

Met Gln Val Leu Asn Thr Met Val Asn Lys His Phe Leu Ser Leu Ser
 1               5                  10                  15

Val Leu Ile Val Leu Leu Gly Leu Ser Ser Asn Leu Thr Ala Gly
             20                  25                  30

<210> SEQ ID NO 9
<211> LENGTH: 3
<212> TYPE: PRT
<213> ORGANISM: Artificial Sequence
<220> FEATURE:
<223> OTHER INFORMATION: Substrate for plasmin
```

-continued

```
<400> SEQUENCE: 9

Glu Phe Lys
1
```

US 7,659,445 B2

EXPRESSION OF PLASMINOGEN AND MICROPLASMINOGEN IN DUCK WEED

CROSS-REFERENCE TO RELATED PATENT APPLICATIONS

This application claims the benefit of U.S. Provisional Patent Application No. 60/543,487, filed Feb. 11, 2004, which is hereby incorporated in its entirety by reference herein.

FIELD OF THE INVENTION

The present invention relates to recombinant protein production systems. More specifically, the invention is directed to methods and compositions for use in the expression of recombinant plasminogen and recombinant microplasminogen in duckweed.

BACKGROUND OF THE INVENTION

The duckweeds are the sole members of the monocotyledonous family Lemnaceae. The five genera and 38 species are all small, free-floating, fresh-water plants whose geographical range spans the entire globe (Landolt (1986) *Biosystematic Investigation on the Family of Duckweeds: The Family of Lemnaceae—A Monograph Study* Geobatanischen Institut ETH, Stiftung Rubel, Zurich). Although the most morphologically reduced plants known, most duckweed species have all the tissues and organs of much larger plants, including roots, stems, flowers, seeds and fronds. Duckweed species have been studied extensively and a substantial literature exists detailing their ecology, systematics, life-cycle, metabolism, disease and pest susceptibility, their reproductive biology, genetic structure, and cell biology. (Hillman (1961) *Bot. Review* 27: 221; Landolt (1986) *Biosystematic Investigation on the Family of Duckweeds: The Family of Lemnaceae—A Monograph Study* Geobatanischen Institut ETH, Stiftung Rubel, Zurich).

The growth habit of the duckweeds is ideal for microbial culturing methods. The plant rapidly proliferates through vegetative budding of new fronds, in a macroscopic manner analogous to asexual propagation in yeast. This proliferation occurs by vegetative budding from meristematic cells. The meristematic region is small and is found on the ventral surface of the frond. Meristematic cells lie in two pockets, one on each side of the frond midvein. The small midvein region is also the site from which the root originates and the stem arises that connects each frond to its mother frond. The meristematic pocket is protected by a tissue flap. Fronds bud alternately from these pockets. Doubling times vary by species and are as short as 20-24 hours (Landolt (1957) *Ber. Schweiz. Bot. Ges.* 67: 271; Chang et al. (1977) *Bull. Inst. Chem. Acad. Sin.* 24:19; Datko and Mudd (1970) *Plant Physiol.* 65:16; Venkataraman et al. (1970) *Z. Pflanzenphysiol.* 62: 316).

Intensive culture of duckweed results in the highest rates of biomass accumulation per unit time (Landolt and Kandeler (1987) *The Family of Lemnaceae—A Monographic Study Vol. 2: Phytochemistry, Physiology, Application, Bibliography*, Veroffentlichungen des Geobotanischen Institutes ETH, Stiftung Rubel, Zurich), with dry weight accumulation ranging from 6-15% of fresh weight (Tillberg et al. (1979) *Physiol. Plant.* 46:5; Landolt (1957) *Ber. Schweiz. Bot. Ges.* 67:271; Stomp, unpublished data). Protein content of a number of duckweed species grown under varying conditions has been reported to range from 15-45% dry weight (Chang et al (1977) *Bull. Inst. Chem. Acad. Sin.* 24:19; Chang and Chui (1978) *Z. Pflanzenphysiol.* 89:91; Porath et al. (1979) *Aquatic Botany* 7:272; Appenroth et al. (1982) *Biochem. Physiol. Pflanz.* 177:251). Using these values, the level of protein production per liter of medium in duckweed is on the same order of magnitude as yeast gene expression systems.

Duckweed plant or duckweed nodule cultures can be efficiently transformed with an expression cassette containing a nucleotide sequence of interest by any one of a number of methods including *Agrobacterium*-mediated gene transfer, ballistic bombardment, or electroporation. Stable duckweed transformants can be isolated by transforming the duckweed cells with both the nucleotide sequence of interest and a gene that confers resistance to a selection agent, followed by culturing the transformed cells in a medium containing the selection agent. See U.S. Pat. No. 6,040,498 to Stomp et al.

A duckweed gene expression system provides the pivotal technology that would be useful for a number of research and commercial applications. For plant molecular biology research as a whole, a differentiated plant system that can be manipulated with the laboratory convenience of yeast provides a very fast system in which to analyze the developmental and physiological roles of isolated genes. For commercial production of valuable polypeptides, a duckweed-based system has a number of advantages over existing microbial or cell culture systems. Plants demonstrate post-translational processing that is similar to mammalian cells, overcoming one major problem associated with the microbial cell production of biologically active mammalian polypeptides, and it has been shown by others (Hiatt (1990) *Nature* 334:469) that plant systems have the ability to assemble multi-subunit proteins, an ability often lacking in microbial systems. Scale-up of duckweed biomass to levels necessary for commercial production of recombinant proteins is faster and more cost efficient than similar scale-up of mammalian cells, and unlike other suggested plant production systems, e.g., soybeans and tobacco, duckweed can be grown in fully contained and controlled biomass production vessels, making the system's integration into existing protein production industrial infrastructure far easier.

Accordingly, there remains a need for optimized methods and compositions for expressing proteins of interest in duckweed.

SUMMARY OF THE INVENTION

The present invention provides methods and compositions for the production of recombinant plasminogen, microplasminogen, and fragments thereof in a duckweed expression system. The duckweed expression system of the present invention is optimized to produce high levels of plasminogen, microplasminogen, and fragments thereof. The duckweed-produced plasminogen and microplasminogen can be activated to produce a polypeptide having protease activity. Thus, the invention encompasses methods for the expression of plasminogen and microplasminogen in duckweed, duckweed plants that are transformed with expression cassettes for the expression of plasminogen and microplasminogen, and nucleic acids comprising nucleotide sequences encoding plasminogen and microplasminogen, where these nucleotide sequences are modified to enhance their expression in duckweed.

Accordingly, in one embodiment, the present invention provides a method for producing plasminogen in duckweed, wherein said method comprises the steps of culturing a duckweed plant or duckweed plant cell, where the duckweed plant or duckweed plant cell is stably transformed with a nucleic acid molecule comprising a nucleotide sequence encoding plasminogen; and collecting the plasminogen from said duckweed plant or duckweed plant cell. In some embodiments, the nucleotide sequence encoding plasminogen is operably linked to a nucleotide sequence encoding a signal peptide.

In another embodiment, the present invention provides a method for producing microplasminogen in duckweed, where the method comprises the steps of culturing within a duckweed culture medium a duckweed plant culture or a duckweed nodule culture, where the duckweed plant culture or the duckweed nodule culture is stably transformed with a nucleic acid molecule comprising a nucleotide sequence encoding microplasminogen and an operably linked coding sequence for a signal peptide that directs secretion of the microplasminogen into the culture medium; and collecting the microplasminogen from the duckweed culture medium.

The invention also encompasses duckweed plants, duckweed nodules, and duckweed plant cells transformed with expression cassettes capable of expressing plasminogen or microplasminogen in duckweed. Also provided are nucleic acid molecules comprising a nucleotide sequence encoding plasminogen or microplasminogen, where the nucleotide sequences comprise duckweed-optimized codons.

These and other aspects of the present invention are disclosed in more detail in the description of the invention given below.

DETAILED DESCRIPTION OF THE INVENTION

Figure 1:
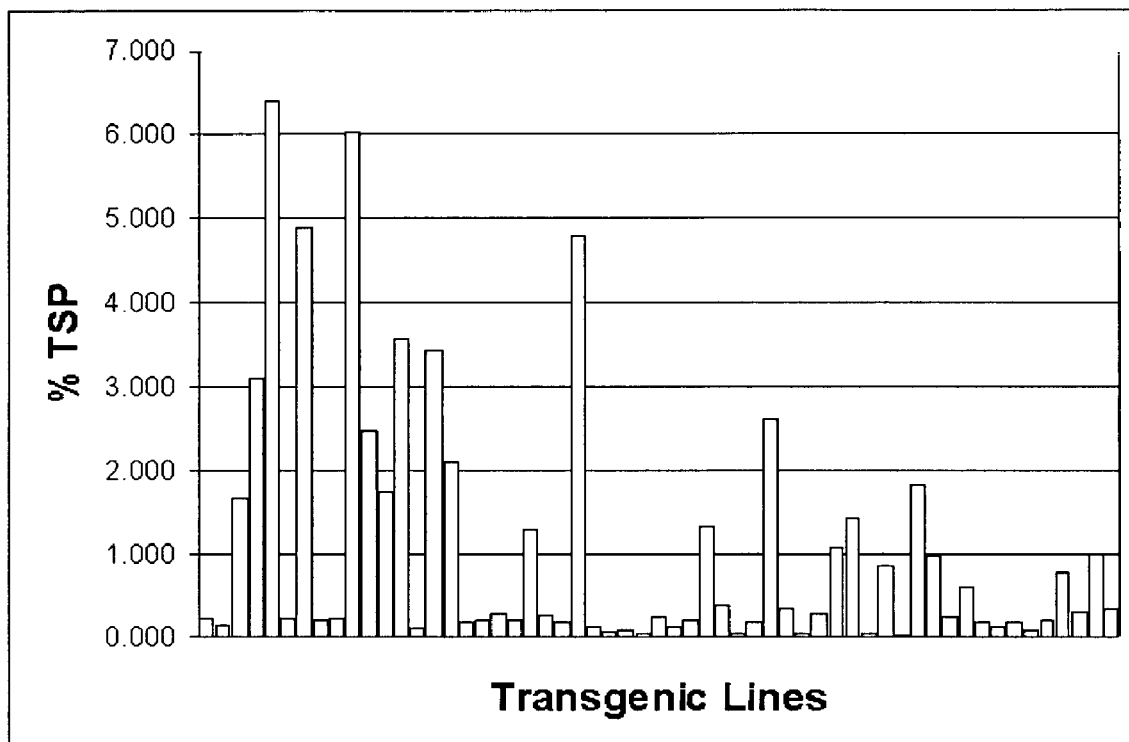
FIG. 1 shows the level of plasminogen in tissue homogenates measured by ELISA in 56 duckweed lines that were transformed with the plasminogen expression construct BAP01. The level of plasminogen is expressed as a percentage of the total soluble protein in the homogenates. See Example 1 in the Experimental section for additional details.

The present invention is drawn to methods and compositions for the production of recombinant plasminogen, microplasminogen, and fragments thereof in a duckweed expression system. It is the novel finding of the present invention that a duckweed expression system may be used to produce high levels of plasminogen and microplasminogen. The duckweed-produced plasminogen and microplasminogen can be activated to produce a polypeptide having protease activity.

Plasminogen is the inactive precursor form of plasmin, the principal fibrinolytic enzyme in mammals. Plasmin also plays an important role in cell migration, tissue remodeling, and bacterial invasion. Plasmin is a serine protease that preferentially cleaves Lys-|-Xaa and Arg-|-Xaa bonds with higher selectivity than trypsin. Plasminogen activators such as tissue plasminogen activator (tPA) or urokinase cleave human plasminogen molecule at the $Arg_{560}$-$Val_{561}$, bond to produce active plasmin. The two resulting chains of plasmin are held together by two interchain disulphide bridges. The light chain (25 kDa) carries the catalytic center (which comprises the catalytic triad) and shares sequence similarity with trypsin and other serine proteases. The heavy chain (60 kDa) consists of five highly similar triple-loop structures called kringles. Some of the kringles contain lysine binding sites that mediates the plasminogen/plasmin interaction with fibrin. Plasmin belongs to peptidase family S1.

Microplasminogen consists of the proenzyme domain of plasminogen with a stretch of connecting peptide and a few residues of kringle 5 attached at its N-terminal end. It is produced by the action of plasmin on plasminogen. See, for example, Shi et al. (1980) *J. Biol. Chem.* 263:17071-5. Like plasminogen, microplasminogen is activated by tPA and urokinase to form a proteolytically active molecule. Human microplasmin has a molecular weight of approximately 29 kDa and has a lower affinity for fibrin when compared with plasmin.

Plasmin and microplasmin are proposed for use in thrombolytic therapy in a number of applications including the treatment of myocardial infarction, occlusive stroke, deep venous thrombosis, and peripheral arterial diseases. See, for example, U.S. Pat. No. 5,407,673, U.S. Pat. No. 6,355,243, U.S. Patent Application No. 20030175264, Lapchak et al. (2002) *Stroke* 33:2279-2284, and Nagai et al. (2003) *J. Thromb. Haemost.* 1:307-13, each of which is herein incorporated by reference in its entirety. One goal of using plasmin and microplasmin in such therapy is to avoid the side effects of therapy using plasminogen activators such as tPA, urokinase, and streptokinase. Such side effects include gastrointestinal and intercranial hemorrhage. However, the use of plasmin and microplasmin as therapeutic agents has been limited in part by the difficulty of producing large quantities of stable plasminogen and microplasminogen precursor proteins.

Although expression of large amounts of plasminogen in a recombinant system is a convenient way to obtain plasminogen for use in thrombolytic therapy, there have been great difficulties in expression of intact human plasminogen in expression systems due to the nearly ubiquitous presence of intracellular plasminogen activators in mammalian cell types. The presence of these activators results in the degradation of the produced plasminogen. See, for example, Busy et al. (1988) *Fibrinolysis* 2:64.

The present invention solves this problem by providing an expression system capable of expressing high levels of stable plasminogen and microplasminogen. Thus, in one embodiment, the present invention provides a method for producing plasminogen in duckweed, wherein said method comprises the steps of culturing a duckweed plant or duckweed plant cell, where the duckweed plant or duckweed plant cell is stably transformed with a nucleic acid molecule comprising a nucleotide sequence encoding plasminogen; and collecting the plasminogen from said duckweed plant or duckweed plant cell. The nucleotide sequence encoding plasminogen may be operably linked to a nucleotide sequence encoding a signal peptide.

The methods of the invention may be used to express high levels of plasminogen in duckweed. Thus, in some embodiments of the method, at least about 1%, at least about 2%, at least about 3%, at least about 4%, at least about 5%, at least about 6%, at least about 7%, or at least about 8% of the soluble protein in the duckweed plant or duckweed plant cell is plasminogen.

The present invention also provides an improvement in a method of producing stable plasminogen in duckweed, wherein the improvement comprises producing the plasminogen in duckweed. The *Lemna*-produced plasminogen is stable and loses less than 10% of its activity when stored overnight in a *Lemna* tissue extract. The *Lemna*-produced plasminogen also undergoes less than 10% degradation in *Lemna* tissue extracts following a freeze-thaw cycle.

In another embodiment, the present invention provides a method for producing microplasminogen in duckweed, where the method comprises the steps of culturing within a duckweed culture medium a duckweed plant culture or a duckweed nodule culture, where the duckweed plant culture or the duckweed nodule culture is stably transformed with a nucleic acid molecule comprising a nucleotide sequence encoding microplasminogen and an operably linked coding sequence for a signal peptide that directs secretion of the microplasminogen into the culture medium; and collecting the microplasminogen from the duckweed culture medium.

The methods of the invention may be used to express high levels of microplasminogen in duckweed. Thus, in some embodiments of the method, the, duckweed culture medium contains at least about 1 mg/L, at least about 2 mg/L, at least about 5 mg/L microplasminogen, at least about 10 mg/L microplasminogen, at least about 15 mg/L microplasminogen, or at least about 20 mg/L microplasminogen as determined by quantitative Western blotting.

The present invention provides a method for producing a plasminogen fragment in duckweed, wherein said method comprises the steps of culturing a duckweed plant or duckweed plant cell, where the duckweed plant or duckweed plant cell is stably transformed with a nucleic acid molecule comprising a nucleotide sequence encoding the plasminogen fragment; and collecting the plasminogen fragment from the duckweed plant, the duckweed plant cell, or the duckweed culture medium. The nucleotide sequence encoding plasminogen may be operably linked to a nucleotide sequence encoding a signal peptide.

In some embodiments of the methods of the present invention, the nucleic acid molecule comprising the nucleotide sequence encoding plasminogen, microplasminogen, or fragment thereof is modified to enhance its expression in duckweed. Examples of such modifications include the use of duckweed-preferred codons in the coding sequence for the plasminogen microplasminogen, the use of an operably linked nucleotide sequence comprising a plant intron that is inserted upstream of the coding sequence; and the use of a leader sequence that increases the translation of the nucleotide sequence encoding plasminogen or microplasminogen. In some embodiments, two or more of these modifications are used in combination. Where the nucleotide sequence encoding plasminogen is operably linked to a nucleotide sequence encoding a signal peptide, the nucleotide sequence encoding the signal peptide may also comprise duckweed-preferred codons.

The invention also encompasses duckweed plants, duckweed nodules, and duckweed plant cells transformed with expression cassettes capable of expressing plasminogen or microplasminogen in duckweed. Also provided are nucleic acid molecules comprising a nucleotide sequence encoding plasminogen or microplasminogen, where the nucleotide sequences comprise duckweed-optimized codons.

DEFINITIONS

"Polypeptide" refers to any monomeric or multimeric protein or peptide.

"Biologically active polypeptide" refers to a polypeptide that has the capability of performing one or more biological functions or a set of activities normally attributed to the polypeptide in a biological context. Within the context of a protease precursor such as plasminogen or microplasminogen, biological activity encompasses the capability of the polypeptide to be activated to produce a proteolytically active molecule. Proteolytic activity of plasminogen or microplasminogen following activation may be measured by any assay known in the art, including the assay based on the use of a chromogenic substrate as described elsewhere herein.

The terms "expression" or "production" refer to the biosynthesis of a gene product, including the transcription, translation, and assembly of said gene product.

The term "duckweed" refers to members of the family Lemnaceae. This family currently is divided into five genera and 38 species of duckweed as follows: genus *Lemna* (*L. aequinoctialis, L. disperma, L. ecuadoriensis, L. gibba, L. japonica, L. minor, L. miniscula, L. obscura, L. perpusilla, L. tenera, L. trisulca, L. turionifera, L. valdiviana*); genus *Spirodela* (*S. intermedia, S. polyrrhiza, S. punctata*); genus *Wolffia* (*Wa. angusta, Wa. arrhiza, Wa. australina, Wa. borealis, Wa. brasiliensis, Wa. columbiana, Wa. elongata, Wa. globosa, Wa. microscopica, Wa. neglecta*); genus *Wolfiella* (*Wl. caudata, Wl. denticulata, Wl. gladiata, Wl. hyalina, Wl. lingulata, Wl. repunda, Wl. rotunda, and Wl. neotropica*) and genus *Landoltia* (*L. punctata*). Any other genera or species of Lemnaceae, if they exist, are also aspects of the present invention. *Lemna* species can be classified using the taxonomic scheme described by Landolt (1986) *Biosystematic Investigation on the Family of Duckweeds: The family of Lemnaceae—A Monograph Study* Geobatanischen Institut ETH, Stiftung Rubel, Zurich.

The term "duckweed nodule culture" as used herein refers to a culture comprising duckweed cells wherein at least about 50%, 55%, 60%, 65%, 70%, 75%, 80%, 85%, 90%, 95%, or 100% of the cells are differentiated cells. A "differentiated cell," as used herein, is a cell with at least one phenotypic characteristic (e.g., a distinctive cell morphology or the expression of a marker nucleic acid or protein) that distinguishes it from undifferentiated cells or from cells found in other tissue types. The differentiated cells of the duckweed nodule culture described herein form a tiled smooth surface of interconnected cells fused at their adjacent cell walls, with nodules that have begun to organize into frond primordium scattered throughout the tissue. The surface of the tissue of the nodule culture has epidermal cells connect to each other via plasmadesmata.

"Duckweed-preferred codons" as used herein refers to codons that have a frequency of codon usage in duckweed of greater than 17%.

"*Lemna*-preferred codons" as used herein refers to codons that have a frequency of codon usage in the genus *Lemna* of greater than 17%.

"*Lemna gibba*-preferred codons" as used herein refers to codons that have a frequency of codon usage in *Lemna gibba* of greater than 17%.

"Translation initiation codon" refers to the codon that initiates the translation of the mRNA transcribed from the nucleotide sequence of interest.

"Translation initiation context nucleotide sequence" as used herein refers to the identity of the three nucleotides directly 5' of the translation initiation codon.

"Secretion" as used herein refers to translocation of a polypeptide across the plasma membrane of a host plant cell. In some embodiments of the present invention, the polypeptide is retained within the apoplast, the region between the plasma membrane and the cell wall. In other embodiments, the polypeptide is translocated across cell wall of the plant host cell.

"Operably linked" as used herein in reference to nucleotide sequences refers to multiple nucleotide sequences that are placed in a functional relationship with each other. Generally, operably linked DNA sequences are contiguous and, where necessary to join two protein coding regions, in reading frame.

A. Expression Cassettes

According to the present invention, stably transformed duckweed is obtained by transformation with an expression cassette comprising a nucleotide sequence encoding plasminogen or a nucleotide sequence encoding microplasminogen. The expression cassette comprises a transcriptional initiation region linked to the nucleic acid or gene of interest. Such an expression cassette is provided with a plurality of restriction sites for insertion of the nucleotide sequence encoding the protein of interest to be under the transcriptional regulation of the regulatory regions. The expression cassette may encode a single gene of interest. In particular embodiments of the invention, the nucleic acid to be transferred contains two or more expression cassettes, each of which encodes at least one gene of interest.

The transcriptional initiation region, (e.g., a promoter) may be native or homologous or foreign or heterologous to the host, or could be the natural sequence or a synthetic sequence. By foreign, it is intended that the transcriptional initiation region is not found in the wild-type host into which the transcriptional initiation region is introduced. As used herein a chimeric gene comprises a coding sequence operably linked to a transcription initiation region that is heterologous to the coding sequence.

Any suitable promoter known in the art can be employed according to the present invention (including bacterial, yeast, fungal, insect, mammalian, and plant promoters). For example, plant promoters, including duckweed promoters, may be used. Exemplary promoters include, but are not limited to, the Cauliflower Mosaic Virus 35S promoter, the opine synthetase promoters (e.g., nos, mas, ocs, etc.), the ubiquitin promoter, the actin promoter, the ribulose bisphosphate (RubP) carboxylase small subunit promoter, and the alcohol dehydrogenase promoter. The duckweed RubP carboxylase small subunit promoter is known in the art (Silverthorne et al. (1990) *Plant Mol. Biol.* 15:49). Other promoters from viruses that infect plants, preferably duckweed, are also suitable including, but not limited to, promoters isolated from Dasheen mosaic virus, *Chlorella* virus (e.g., the *Chlorella* virus adenine methyltransferase promoter; Mitra et al. (1994) *Plant Mol. Biol.* 26:85), tomato spotted wilt virus, tobacco rattle virus, tobacco necrosis virus, tobacco ring spot virus, tomato ring spot virus, cucumber mosaic virus, peanut stump virus, alfalfa mosaic virus, sugarcane baciliform badnavirus and the like.

Finally, promoters can be chosen to give a desired level of regulation. For example, in some instances, it may be advantageous to use a promoter that confers constitutive expression (e.g, the mannopine synthase promoter from *Agrobacterium tumefaciens*). Alternatively, in other situations, it may be advantageous to use promoters that are activated in response to specific environmental stimuli (e.g., heat shock gene promoters, drought-inducible gene promoters, pathogen-inducible gene promoters, wound-inducible gene promoters, and light/dark-inducible gene promoters) or plant growth regulators (e.g., promoters from genes induced by abscissic acid, auxins, cytokinins, and gibberellic acid) or other compounds such as ethanol or ethylene. As a further alternative, promoters can be chosen that give tissue-specific expression (e.g., root, leaf, and floral-specific promoters).

The overall strength of a given promoter can be influenced by the combination and spatial organization of cis-acting nucleotide sequences such as upstream activating sequences. For example, activating nucleotide sequences derived from the *Agrobacterium tumefaciens* octopine synthase gene can enhance transcription from the *Agrobacterium tumefaciens* mannopine synthase promoter (see U.S. Pat. No. 5,955,646 to Gelvin et al.). In the present invention, the expression cassette can contain activating nucleotide sequences inserted upstream of the promoter sequence to enhance the expression of the nucleotide sequence of interest. In one embodiment, the expression cassette includes three upstream activating sequences derived from the *Agrobacterium tumefaciens* octopine synthase gene operably linked to a promoter derived from an *Agrobacterium tumefaciens* mannopine synthase gene (see U.S. Pat. No. 5,955,646, herein incorporated by reference).

The transcriptional cassette includes in the 5'-3' direction of transcription, a transcriptional and translational initiation region, a nucleotide sequence of interest, and a transcriptional and translational termination region functional in plants. Any suitable termination sequence known in the art may be used in accordance with the present invention. The termination region may be native with the transcriptional initiation region, may be native with the nucleotide sequence of interest, or may be derived from another source. Convenient termination regions are available from the Ti-plasmid of *A. tumefaciens*, such as the octopine synthetase and nopaline synthetase termination regions. See also Guerineau et al. (1991) *Mol. Gen. Genet.* 262:141; Proudfoot (1991) *Cell* 64:671; Sanfacon et al. (1991) *Genes Dev.* 5:141; Mogen et al. (1990) *Plant Cell* 2:1261; Munroe et al. (1990) *Gene* 91:151; Ballas et al. (1989) *Nucleic Acids Res.* 17:7891; and Joshi et al. (1987) *Nucleic Acids Res.* 15:9627. Additional exemplary termination sequences are the pea RubP carboxylase small subunit termination sequence and the Cauliflower Mosaic Virus 35S termination sequence and the ubiquitin terminator from many plant species. Other suitable termination sequences will be apparent to those skilled in the art.

The expression cassettes may contain more than one gene or nucleic acid sequence to be transferred and expressed in the transformed plant. Thus, each nucleic acid sequence will be operably linked to 5' and 3' regulatory sequences. Alternatively, multiple expression cassettes may be provided.

Generally, the expression cassette will comprise a selectable marker gene for the selection of transformed cells or tissues. Selectable marker genes include genes encoding antibiotic resistance, such as those encoding neomycin phosphotransferase II (NEO), neomycin phosphotransferase III and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See DeBlock et al. (1987) *EMBO J.* 6:2513; DeBlock et al. (1989) *Plant Physiol.* 91:691; Fromm et al. (1990) *BioTechnology* 8:833; Gordon-Kamm et al. (1990) *Plant Cell* 2:603; and Frisch et al. (1995) *Plant Mol. Biol.* 27:405-9. For example, resistance to glyphosate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

For purposes of the present invention, selectable marker genes include, but are not limited to, genes encoding neomycin phosphotransferase II (Fraley et al. (1986) *CRC Critical Reviews in Plant Science* 4:1), neomycin phosphotransferase III (Frisch et al. (1995) *Plant Mol. Biol.* 27:405-9), cyanamide hydratase (Maier-Greiner et al. (1991) *Proc. Natl. Acad. Sci. USA* 88:4250); aspartate kinase; dihydrodipicolinate synthase (Perl et al. (1993) *BioTechnology* 11:715); bar gene (Toki et al. (1992) *Plant Physiol.* 100:1503; Meagher et al. (1996) *Crop Sci.* 36:1367); tryptophan decarboxylase (Goddijn et al. (1993) *Plant Mol. Biol.* 22:907); neomycin phosphotransferase (NEO; Southern et al. (1982) *J. Mol. Appl. Gen.* 1:327); hygromycin phosphotransferase (HPT or HYG; Shimizu et al. (1986) *Mol. Cell. Biol.* 6:1074); dihydrofolate reductase (DHFR; Kwok et al. (1986) *Proc. Natl. Acad. Sci. USA* 83:4552); phosphinothricin acetyltransferase (DeBlock et al. (1987) *EMBO J.* 6:2513); 2,2-dichloropropionic acid dehalogenase (Buchanan-Wollatron et al. (1989) *J. Cell. Biochem.* 13D:330); acetohydroxyacid synthase (U.S. Pat. No. 4,761,373 to Anderson et al.; Haughn et al. (1988) *Mol. Gen. Genet.* 221:266); 5-enolpyruvyl-shikimate-phosphate synthase (aroA; Comai et al. (1985) *Nature* 317:741); haloarylnitrilase (WO 87/04181 to Stalker et al.); acetyl-coenzyme A carboxylase (Parker et al. (1990) *Plant Physiol.* 92:1220); dihydropteroate synthase (sulI; Guerineau et al. (1990) *Plant Mol. Biol.* 15:127); and 32 kDa photosystem II polypeptide (psbA; Hirschberg et al. (1983) *Science* 222:1346 (1983).

Also included are genes encoding resistance to: gentamycin (e.g., aacC1, Wohlleben et al. (1989) *Mol. Gen. Genet.* 217:202-208); chloramphenicol (Herrera-Estrella et al. (1983) *EMBO J.* 2:987); methotrexate (Herrera-Estrella et al. (1983) *Nature* 303:209; Meijer et al. (1991) *Plant Mol. Biol.* 16:807); hygromycin (Waldron et al. (1985) *Plant Mol. Biol.* 5:103; Zhijian et al. (1995) *Plant Science* 108:219; Meijer et al. (1991) *Plant Mol. Bio.* 16:807); streptomycin (Jones et al. (1987) *Mol. Gen. Genet.* 210:86); spectinomycin (Bretagne-Sagnard et al. (1996) *Transgenic Res.* 5:131); bleomycin (Hille et al. (1986) *Plant Mol. Biol.* 7:171); sulfonamide (Guerineau et al. (1990) *Plant Mol. Bio.* 15:127); bromoxynil (Stalker et al. (1988) *Science* 242:419); 2,4-D (Streber et al. (1989) *BioTechnology* 7:811); phosphinothricin (DeBlock et al. (1987) *EMBO J.* 6:2513); spectinomycin (Bretagne-Sagnard and Chupeau, *Transgenic Research* 5:131).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. See Yarranton (1992) *Curr. Opin. Biotech.* 3:506; Chistopherson et al. (1992) *Proc. Natl. Acad. Sci. USA* 89:6314; Yao et al. (1992) *Cell* 71:63; Reznikoff (1992) *Mol. Microbiol.* 6:2419; Barkley et al. (1980) *The Operon* 177-220; Hu et al. (1987) *Cell* 48:555; Brown et al. (1987) *Cell* 49:603; Figge et al. (1988) Cell 52:713; Deuschle et al. (1989) *Proc. Natl. Acad. Sci. USA* 86:5400; Fuerst et al. (1989) *Proc. Natl. Acad. Sci. USA* 86:2549; Deuschle et al. (1990) *Science* 248:480; Labow et al. (1990) *Mol. Cell. Biol.* 10:3343; Zambretti et al. (1992) *Proc. Natl. Acad. Sci. USA* 89:3952; Baim et al. (1991) *Proc. Natl. Acad. Sci. USA* 88:5072; Wyborski et al. (1991) *Nuc. Acids Res.* 19:4647; Hillenand-Wissman (1989) *Topics in Mol. And Struc. Biol.* 10:143; Degenkolb et al. (1991) *Antimicrob. Agents Chemother.* 35:1591; Kleinschnidt et al. (1988) *Biochemistry* 27:1094; Gatz et al. (1992) *Plant J.* 2:397; Gossen et al. (1992) *Proc. Natl. Acad. Sci. USA* 89:5547; Oliva et al. (1992) *Antimicrob. Agents Chemother.* 36:913; Hlavka et al. (1985) *Handbook of Experimental Pharmacology* 78; and Gill et al. (1988) *Nature* 334:721. Such disclosures are herein incorporated by reference.

The above list of selectable marker genes are not meant to be limiting. Any lethal or non-lethal selectable marker gene can be used in the present invention.

B. Plasminogen and Microplasminogen

The present invention is directed to methods and compositions for the expression of plasminogen, microplasminogen, and fragments thereof in duckweed. The plasminogen to be expressed in duckweed may be from any mammalian source. In some embodiments, the plasminogen is human or porcine. In a particular embodiment, the plasminogen has the amino acid sequence of the human plasminogen shown in SEQ ID NO:4. In other embodiments, the plasminogen is a biologically active variant of the amino acid sequence shown in SEQ ID NO:4.

Similarly, the microplasminogen to be expressed in duckweed may be from any mammalian source. In some embodiments, the microplasminogen is human or porcine. In a particular embodiment, the microplasminogen has the amino acid sequence of the human microplasminogen shown in SEQ ID NO:6. In other embodiments, the plasminogen is a biologically active variant of the amino acid sequence shown in SEQ ID NO6.

Fragments of plasminogen or microplasminogen may be produced according to the present invention. Such fragments may comprise at least 50, at least 60, at least 70, at least 80, at least 90, at least 95, at least 101, at least 150, at least 200, at least 250, at least 300, at least 350, at least 377, at least 400, at least 450, at least 500, at least 550, at least 600, at least 650, at least 700, or at least 750 contiguous amino acids of a plasminogen protein. Examples of fragments that may be produced according to the invention include miniplasminogen and angiostatin. Non-limiting examples of plasminogen or microplasminogen fragments are given in O'Reilly et al. (1994) *Cell* 79:315-28; Sim et al. (1997) *Cancer Res.*

57:1329-34; U.S. Pat. No. 5,972,896, and U.S. Patent Publications 20020164717, 20020037847, and 20010016644; each of which is herein incorporated by reference in its entirety. In some embodiments, the fragments retain the enzymatic activity, for example the protease activity, of plasminogen or microplasminogen.

A "biologically active variant" of plasminogen or microplasminogen is a polypeptide derived from these polypeptides by deletion (so-called truncation) or addition of one or more amino acids to the N-terminal and/or C-terminal end of the native protein; deletion or addition of one or more amino acids at one or more sites in the protein; or substitution of one or more amino acids at one or more sites in the protein. Biologically active variant plasminogen and microplasminogen polypeptides encompassed by the present invention are biologically active, that is they are capable of being activated to produce a protein having the protease activity of the plasmin family of proteases (Enzyme Class 3.4.21.7). Such biologically active variants may result from, for example, genetic polymorphism or from human manipulation. Biologically active variants of a plasminogen or microplasminogen according to the invention will have at least about 50%, 60%, 65%, 70%, generally at least about 75%, 80%, 85%, preferably at least about 90%, 91%, 92%, 93%, 94%, 95%, 96%, 97%, such as at least about 98%, 99% or more sequence identity to the amino acid sequence shown in SEQ ID NO:4 or SEQ ID NO:6. Thus, a biologically active variant of plasminogen or microplasminogen of the invention may differ from the amino acid sequences shown in SEQ ID NO: 4 and SEQ ID NO:6 by as few as 1-15 amino acid residues, as few as 1-10 amino acid residues, such as 6-10 amino acid residues, as few as 5 amino acid residues, or as few as 4, 3, 2, or even 1 amino acid residue. Examples of biologically active variants of plasminogen are known in the art and are described, for example, in U.S. Pat. No. 5,190,756. In order to retain biological activity, any substitutions will preferably be conservative in nature, and truncations and substitutions will generally made in residues that are not required for protease activity. The residues and domains underlying the activity of plasmin/plasminogen and microplasmin/microplasminogen are known in the art and have been described, for example, in Kolev et al. (1997) *J. Biol. Chem.* 272:13666-675; de los Santos et al. (1997) *Ciba Found. Symp.* 212:66-76, Peisach et al. (1999) *Biochemistry* 38:11180-11188, and Turner et al. (2002) *J. Biol. Chem.* 277:33-68-74); each of which is herein incorporated by reference in its entirety.

The comparison of sequences and determination of percent identity and percent similarity between two sequences can be accomplished using a mathematical algorithm. In a preferred embodiment, the percent identity between two amino acid sequences is determined using the Needleman and Wunsch (1970) *J. Mol. Biol.* 48:444-453 algorithm, which is incorporated into the GAP program in the GCG software package (available at www.accelrys.com), using either a BLOSUM62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a BLOSUM62 scoring matrix (see Henikoff et al. (1989) *Proc. Natl. Acad. Sci. USA* 89:10915) and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity limitation of the invention) is using a BLOSUM62 scoring matrix with a gap weight of 60 and a length weight of 3).

The percent identity between two amino acid or nucleotide sequences can also be determined using the algorithm of E. Meyers and W. Miller (1989) *CABIOS* 4:11-17 which has been incorporated into the ALIGN program (version 2.0), using a PAM120 weight residue table, a gap length penalty of 12 and a gap penalty of 4.

C. Modification of Nucleotide Sequences for Enhanced Expression in Duckweed

In some embodiments, the present invention provides for the modification of the expressed nucleotide sequence to enhance its expression in duckweed. One such modification is the synthesis of the nucleotide sequence encoding plasminogen or microplasminogen using duckweed-preferred codons. Methods are available in the art for synthesizing nucleotide sequences with plant-preferred codons. See, for example, U.S. Pat. Nos. 5,380,831 and 5,436,391; Perlak et al. (1991) *Proc. Natl. Acad. Sci. USA* 15:3324; Iannacome et al. (1997) *Plant Mol. Biol.* 34:485; and Murray et al., (1989) *Nucleic Acids. Res.* 17:477, herein incorporated by reference. The preferred codons may be determined from the codons of highest frequency in the proteins expressed in duckweed. Thus, the frequency of usage of particular a codon in duckweed may be determined by analyzing codon usage in a group of duckweed coding sequences. A number of duckweed coding sequences are known to those of skill in the art; see for example, the sequences contained in the GenBank® database which may be accessed through the website for the National Center for Biotechnology Information, a division of the National Library of Medicine, which is located in Bethesda, Md. Tables showing the frequency of codon usage based on the sequences contained in the most recent GenBank® release may be found on the website for the Kazusa DNA Research Institute in Chiba Japan; see www.kazusa.or.jp/codon/. This database is described in Nakamura et al. (2000) *Nucl. Acids Res.* 28: 292.

It is recognized that genes that have been optimized for expression in duckweed and other monocots can be used in the methods of the invention. See, e.g., EP 0 359 472, EP 0 385 962, WO 91/16432; Perlak et al. (1991) *Proc. Natl. Acad. Sci. USA* 88:3324; Iannacome et al. (1997) *Plant Mol. Biol.* 34:485; and Murray et al. (1989) *Nuc. Acids Res.* 17:477, and the like, herein incorporated by reference. It is further recognized that all or any part of the gene sequence may be optimized or synthetic. In other words, fully optimized or partially optimized sequences may also be used. For example, 40%, 45%, 50%, 55%, 60%, 65%, 70%, 75%, 80%, 85%, 87%, 90%, 91%, 92%, 93%, 94%, 95%, 96%, 97%, 98%, 99%, or 100% of the codons may be duckweed-preferred codons. For example, in some embodiments, the nucleotide sequence encoding plasminogen or microplasminogen comprises between 50-100% duckweed-preferred codons or between 70-100% duckweed preferred codons. In one embodiment, between 90 and 96% of the codons are duckweed-preferred codons. The coding sequence of the nucleotide sequence of interest may comprise codons used with a frequency of at least 17% in duckweed. Codon usage in *Lemna gibba* (Table 1) and *Lemna minor* (Table 2) is shown below. In some embodiments, Table 1 or Table 2 is used to select duckweed preferred codons. In particular embodiments, the duckweed codon optimized sequence encoding plasminogen is the sequence shown in SEQ ID NO:3, and the duckweed codon optimized sequence encoding microplasminogen is the nucleotide sequence shown in SEQ ID NO:5.

TABLE 1

Lemna gibba codon usage from GenBank ® Release 139*

| Amino Acid | Codon | Number | /1000 | Fraction |
|---|---|---|---|---|
| Gly | GGG | 57.00 | 28.89 | 0.35 |
| Gly | GGA | 8.00 | 4.05 | 0.05 |
| Gly | GGT | 3.00 | 1.52 | 0.02 |
| Gly | GGC | 93.00 | 47.14 | 0.58 |
| Glu | GAG | 123.00 | 62.34 | 0.95 |
| Glu | GAA | 6.00 | 3.04 | 0.05 |
| Asp | GAT | 6.00 | 3.04 | 0.08 |
| Asp | GAC | 72.00 | 36.49 | 0.92 |
| Val | GTG | 62.00 | 31.42 | 0.47 |
| Val | GTA | 0.00 | 0.00 | 0.00 |
| Val | GTT | 18.00 | 9.12 | 0.14 |
| Val | GTC | 51.00 | 25.85 | 0.39 |
| Ala | GCG | 44.00 | 22.30 | 0.21 |
| Ala | GCA | 14.00 | 7.10 | 0.07 |
| Ala | GCT | 14.00 | 7.10 | 0.07 |
| Ala | GCC | 139.00 | 70.45 | 0.66 |
| Arg | AGG | 16.00 | 8.11 | 0.15 |
| Arg | AGA | 11.00 | 5.58 | 0.10 |
| Ser | AGT | 1.00 | 0.51 | 0.01 |
| Ser | AGC | 44.00 | 22.30 | 0.31 |
| Lys | AAG | 116.00 | 58.79 | 1.00 |
| Lys | AAA | 0.00 | 0.00 | 0.00 |
| Asn | AAT | 2.00 | 1.01 | 0.03 |
| Asn | AAC | 70.00 | 35.48 | 0.97 |
| Met | ATG | 67.00 | 33.96 | 1.00 |
| Ile | ATA | 4.00 | 2.03 | 0.06 |
| Ile | ATT | 0.00 | 0.00 | 0.00 |
| Ile | ATC | 63.00 | 31.93 | 0.94 |
| Thr | ACG | 19.00 | 9.63 | 0.25 |
| Thr | ACA | 1.00 | 0.51 | 0.01 |
| Thr | ACT | 6.00 | 3.04 | 0.08 |
| Thr | ACC | 50.00 | 25.34 | 0.66 |
| Trp | TGG | 45.00 | 22.81 | 1.00 |
| End | TGA | 4.00 | 2.03 | 0.36 |
| Cys | TGT | 0.00 | 0.00 | 0.00 |
| Cys | TGC | 34.00 | 17.23 | 1.00 |
| End | TAG | 0.00 | 0.00 | 0.00 |
| End | TAA | 7.00 | 3.55 | 0.64 |
| Tyr | TAT | 4.00 | 2.03 | 0.05 |
| Tyr | TAC | 76.00 | 38.52 | 0.95 |
| Leu | TTG | 5.00 | 2.53 | 0.04 |
| Leu | TTA | 0.00 | 0.00 | 0.00 |
| Phe | TTT | 4.00 | 2.03 | 0.04 |
| Phe | TTC | 92.00 | 46.63 | 0.96 |
| Ser | TCG | 34.00 | 17.23 | 0.24 |
| Ser | TCA | 2.00 | 1.01 | 0.01 |
| Ser | TCT | 1.00 | 0.51 | 0.01 |
| Ser | TCC | 59.00 | 29.90 | 0.42 |
| Arg | CGG | 23.00 | 11.66 | 0.22 |
| Arg | CGA | 3.00 | 1.52 | 0.03 |
| Arg | CGT | 2.00 | 1.01 | 0.02 |
| Arg | CGC | 50.00 | 25.34 | 0.48 |
| Gln | CAG | 59.00 | 29.90 | 0.86 |
| Gln | CAA | 10.00 | 5.07 | 0.14 |
| His | CAT | 5.00 | 2.53 | 0.26 |
| His | CAC | 14.00 | 7.10 | 0.74 |
| Leu | CTG | 43.00 | 21.79 | 0.35 |
| Leu | CTA | 2.00 | 1.01 | 0.02 |
| Leu | CTT | 1.00 | 0.51 | 0.01 |
| Leu | CTC | 71.00 | 35.99 | 0.58 |
| Pro | CCG | 44.00 | 22.30 | 0.31 |
| Pro | CCA | 6.00 | 3.04 | 0.04 |
| Pro | CCT | 13.00 | 6.59 | 0.09 |
| Pro | CCC | 80.00 | 40.55 | 0.56 |

TABLE 2

Lemna minor codon usage from GenBank ® Release 139*

| AmAcid | Codon | Number | /1000 | Fraction |
|---|---|---|---|---|
| Gly | GGG | 8.00 | 17.39 | 0.22 |
| Gly | GGA | 11.00 | 23.91 | 0.31 |
| Gly | GGT | 1.00 | 2.17 | 0.03 |
| Gly | GGC | 16.00 | 34.78 | 0.44 |
| Glu | GAG | 25.00 | 54.35 | 0.78 |
| Glu | GAA | 7.00 | 15.22 | 0.22 |
| Asp | GAT | 8.00 | 17.39 | 0.33 |
| Asp | GAC | 16.00 | 34.78 | 0.67 |
| Val | GTG | 21.00 | 45.65 | 0.53 |
| Val | GTA | 3.00 | 6.52 | 0.07 |
| Val | GTT | 6.00 | 13.04 | 0.15 |
| Val | GTC | 10.00 | 21.74 | 0.25 |
| Ala | GCG | 13.00 | 28.26 | 0.32 |
| Ala | GCA | 8.00 | 17.39 | 0.20 |
| Ala | GCT | 6.00 | 13.04 | 0.15 |
| Ala | GCC | 14.00 | 30.43 | 0.34 |
| Arg | AGG | 9.00 | 19.57 | 0.24 |
| Arg | AGA | 11.00 | 23.91 | 0.30 |
| Ser | AGT | 2.00 | 4.35 | 0.05 |
| Ser | AGC | 11.00 | 23.91 | 0.26 |
| Lys | AAG | 13.00 | 28.26 | 0.68 |
| Lys | AAA | 6.00 | 13.04 | 0.32 |
| Asn | AAT | 0.00 | 0.00 | 0.00 |
| Asn | AAC | 12.00 | 26.09 | 1.00 |
| Met | ATG | 9.00 | 19.57 | 1.00 |
| Ile | ATA | 1.00 | 2.17 | 0.08 |
| Ile | ATT | 2.00 | 4.35 | 0.15 |
| Ile | ATC | 10.00 | 21.74 | 0.77 |
| Thr | ACG | 5.00 | 10.87 | 0.28 |
| Thr | ACA | 2.00 | 4.35 | 0.11 |
| Thr | ACT | 2.00 | 4.35 | 0.11 |
| Thr | ACC | 9.00 | 19.57 | 0.50 |
| Trp | TGG | 8.00 | 17.39 | 1.00 |
| End | TGA | 1.00 | 2.17 | 1.00 |
| Cys | TGT | 1.00 | 2.17 | 0.12 |
| Cys | TGC | 7.00 | 15.22 | 0.88 |
| End | TAG | 0.00 | 0.00 | 0.00 |
| End | TAA | 0.00 | 0.00 | 0.00 |
| Tyr | TAT | 1.00 | 2.17 | 0.12 |
| Tyr | TAC | 7.00 | 15.22 | 0.88 |
| Leu | TTG | 3.00 | 6.52 | 0.08 |
| Leu | TTA | 1.00 | 2.17 | 0.03 |
| Phe | TTT | 6.00 | 13.04 | 0.25 |
| Phe | TTC | 18.00 | 39.13 | 0.75 |
| Ser | TCG | 11.00 | 23.91 | 0.26 |
| Ser | TCA | 4.00 | 8.70 | 0.09 |
| Ser | TCT | 6.00 | 13.04 | 0.14 |
| Ser | TCC | 9.00 | 19.57 | 0.21 |
| Arg | CGG | 4.00 | 8.70 | 0.11 |
| Arg | CGA | 4.00 | 8.70 | 0.11 |
| Arg | CGT | 0.00 | 0.00 | 0.00 |
| Arg | CGC | 9.00 | 19.57 | 0.24 |
| Gln | CAG | 11.00 | 23.91 | 0.73 |
| Gln | CAA | 4.00 | 8.70 | 0.27 |
| His | CAT | 0.00 | 0.00 | 0.00 |
| His | CAC | 6.00 | 13.04 | 1.00 |
| Leu | CTG | 9.00 | 19.57 | 0.24 |
| Leu | CTA | 4.00 | 8.70 | 0.11 |
| Leu | CTT | 4.00 | 8.70 | 0.11 |
| Leu | CTC | 17.00 | 36.96 | 0.45 |
| Pro | CCG | 8.00 | 17.39 | 0.29 |
| Pro | CCA | 7.00 | 15.22 | 0.25 |
| Pro | CCT | 5.00 | 10.87 | 0.18 |
| Pro | CCC | 8.00 | 17.39 | 0.29 |

Other modifications can also be made to the nucleotide sequence of interest to enhance its expression in duckweed. These modifications include, but are not limited to, elimination of sequences encoding spurious polyadenylation signals, exon-intron splice site signals, transposon-like repeats, and other such well characterized sequences which may be deleterious to gene expression. The G-C content of the sequence may be adjusted to levels average for a given cellular host, as calculated by reference to known genes expressed in the host cell. When possible, the sequence may be modified to avoid predicted hairpin secondary mRNA structures.

There are known differences between the optimal translation initiation context nucleotide sequences for translation initiation codons in animals and plants and the composition of these translation initiation context nucleotide sequence can influence the efficiency of translation initiation. See, for example, Lukaszewicz et al. (2000) *Plant Science* 154:89-98; and Joshi et al. (1997); *Plant Mol. Biol.* 35:993-1001. In the present invention, the translation initiation context nucleotide sequence for the translation initiation codon of the nucleotide sequence of interest may be modified to enhance expression in duckweed. In one embodiment, the nucleotide sequence is modified such that the three nucleotides directly upstream of the translation initiation codon of the nucleotide sequence of interest are "ACC." In a second embodiment, these nucleotides are "ACA."

Expression of a transgene in duckweed can also be enhanced by the use of 5' leader sequences. Such leader sequences can act to enhance translation. One or more leader sequences may be used in combination to enhance expression of the target nucleotide sequence. Translation leaders are known in the art and include, but are not limited to, picornavirus leaders, e.g., EMCV leader (Encephalomyocarditis 5' noncoding region; Elroy-Stein et al. (1989) *Proc. Natl. Acad. Sci USA* 86:6126); potyvirus leaders, e.g., TEV leader (Tobacco Etch Virus; Allison et al. (1986) *Virology* 154:9); human immunoglobulin heavy-chain binding protein (BiP; Macajak and Sarnow (1991) *Nature* 353:90); untranslated leader from the coat protein mRNA of alfalfa mosaic virus (AMV RNA 4; Jobling and Gehrke (1987) *Nature* 325:622); tobacco mosaic virus leader (TMV; Gallie (1989) *Molecular Biology of RNA*, 23:56); potato etch virus leader (Tomashevskaya et al. (1993) *J. Gen. Virol.* 74:2717-2724); Fed-1 5' untranslated region (Dickey (1992) *EMBO J.* 11:2311-2317); RbcS 5' untranslated region (Silverthorne et al. (1990) *J. Plant. Mol. Biol.* 15:49-58); and maize chlorotic mottle virus leader (MCMV; Lommel et al. (1991) *Virology* 81:382). See also, Della-Cioppa et al. (1987) *Plant Physiology* 84:965. Leader sequence comprising plant intron sequence, including intron sequence from the maize dehydrogenase 1 gene, the castor bean catalase gene, or the *Arabidopsis* tryptophan pathway gene PAT1 has also been shown to increase translational efficient in plants (Callis et al. (1987) *Genes Dev.* 1:1183-1200; Mascarenhas et al. (1990) *Plant Mol. Biol.* 15:913-920). In one embodiment of the present invention, nucleotide sequence corresponding to nucleotides 1222-1775 of the maize alcohol dehydrogenase 1 gene (GenBank Accession Number X04049), set forth in SEQ ID NO: 1, is inserted upstream of the nucleotide sequence of interest to enhance the efficiency of its translation. In another embodiment, the expression vector contains the leader from the *Lemna gibba* ribulose-bis-phosphate carboxylase small subunit 5B gene (Buzby et al. (1990) *Plant Cell* 2:805-814).

It is recognized that any of the duckweed expression-enhancing nucleotide sequence modifications described above can be used in the present invention, including any single modification or any possible combination of modifications. The phrase "modified for enhanced expression in duckweed" as used herein refers to a nucleotide sequence that contains any one or any combination of these modifications.

D. Signal Peptides

Secreted proteins are usually translated from precursor polypeptides that include a "signal peptide" that interacts with a receptor protein on the membrane of the endoplasmic reticulum (ER) to direct the translocation of the growing polypeptide chain across the membrane and into the endoplasmic reticulum for secretion from the cell. This signal peptide is often cleaved from the precursor polypeptide to produce a "mature" polypeptide lacking the signal peptide. In an embodiment of the present invention, a biologically active polypeptide is expressed in duckweed from a nucleotide sequence that is operably linked with a nucleotide sequence encoding a signal peptide that directs secretion of the polypeptide into the culture medium. Plant signal peptides that target protein translocation to the endoplasmic reticulum (for secretion outside of the cell) are known in the art. See, for example, U.S. Pat. No. 6,020,169 to Lee et al. In the present invention, any plant signal peptide can be used to in target polypeptide expression to the ER. In some embodiments, the signal peptide is the *Arabidopsis thaliana* basic endochitinase signal peptide, the extensin signal peptide (Stiefel et al. (1990) *Plant Cell* 2:785-793), or the rice α-amylase signal peptide (SEQ ID NO:8; amino acids 1-31 of NCBI Protein Accession No. AAA33885). In another embodiment, the signal peptide corresponds to the signal peptide of a secreted duckweed protein.

Alternatively, a mammalian signal peptide can be used to target recombinant polypeptides expressed in genetically engineered duckweed for secretion. It has been demonstrated that plant cells recognize mammalian signal peptides that target the endoplasmic reticulum, and that these signal peptides can direct the secretion of polypeptides not only through the plasma membrane but also through the plant cell wall. See U.S. Pat. Nos. 5,202,422 and 5,639,947 to Hiatt et al.

In some embodiment, the nucleotide sequence encoding the signal peptide is modified for enhanced expression in duckweed, utilizing any modification or combination of modifications disclosed in section B above for the nucleotide sequence of interest. For example, a duckweed optimized sequence encoding the signal peptide from rice α-amylase is shown in SEQ ID NO:7. This sequence contains approximately 93% duckweed preferred codons.

The secreted polypeptide can be harvested from the culture medium by any conventional means known in the art and purified by chromatography, electrophoresis, dialysis, solvent-solvent extraction, and the like.

E. Transformed Duckweed Plants and Duckweed Nodule Cultures

The stably transformed duckweed utilized in this invention can be obtained by any method known in the art. In one embodiment, the stably transformed duckweed is obtained by one of the gene transfer methods disclosed in U.S. Pat. No. 6,040,498 or U.S. Patent Publication Numbers 20030115640, 20030033630, or 20020088027; each of which is herein incorporated by reference. These methods include gene transfer by ballistic bombardment with microprojectiles coated with a nucleic acid comprising the nucleotide sequence of interest, gene transfer by electroporation, and gene transfer mediated by *Agrobacterium* comprising a vector comprising the nucleotide sequence of interest. In some embodiments, the stably transformed duckweed is obtained via any one of the *Agrobacterium*-mediated methods disclosed in U.S. Pat. No. 6,040,498 to Stomp et al. The *Agrobacterium* used is *Agrobacterium tumefaciens* or *Agrobacterium rhizogenes*.

Stably transformed duckweed plants may also be obtained by chloroplast transformation. See, for example, U.S. provisional patent application No. 60/492,179, filed Aug. 1, 2003, entitled "Chloroplast transformation of duckweed." Stably transformed duckweed lines may also be produced using plant virus expression vectors. See, for example, U.S. Pat. No. 6,632,980 and Koprowski and Yusibov (2001) *Vaccine* 19:2735-2741.

It is preferred that the stably transformed duckweed plants utilized in these methods exhibit normal morphology and are fertile by sexual reproduction. Preferably, transformed plants of the present invention contain a single copy of the transferred nucleic acid, and the transferred nucleic acid has no notable rearrangements therein. Also preferred are duckweed plants in which the transferred nucleic acid is present in low copy numbers (i.e., no more than twelve copies, no more than eight copies, no more than five copies, alternately, no more than three copies, as a further alternative, fewer than three copies of the nucleic acid per transformed cell).

EXPERIMENTAL

The following examples are offered for purposes of illustration, not by way of limitation.

Expression Constructs for the Production of Plasminogen and Microplasminogen in Duckweed The expression vector used in the present examples is a modified version of pBMSP-1, which is described in U.S. Pat. No. 5,955,646, herein incorporated by reference. The transcriptional cassette of the vector contained three copies of a transcriptional activating nucleotide sequence derived from the *Agrobacterium tumefaciens* octopine synthase and, an additional transcriptional activating nucleotide sequence derived from the *Agrobacterium tumefaciens* mannopine synthase gene, a promoter region derived from the *Agrobacterium tumefaciens* mannopine synthase gene, a polylinker site for insertion of the nucleotide sequence encoding the polypeptide of interest, and a termination sequence derived from the *Agrobacterium tumefaciens* nopaline synthase gene (see, van Engelen et al. (1995) 4:288-290; Ni et al. (1995) *Plant J.* 7:661-76; and Luehrsen et al. (1991) *Mol. Gen. Genet.* 225:81-93, each of which is herein incorporated by reference).

The expression vector also contained a nucleotide sequence coding for gentamycin acetyltransferase-3-I, aacC1, Wohlleben et al. (1989) *Mol. Gen. Genet.* 217:202-208) encoding gentamycin resistance as a selectable marker. Transcription of the selectable marker sequence is driven by a promoter derived from the *Agrobacterium tumefaciens* nopaline synthase II gene.

The expression vector additionally contains the leader from the ribulose-bis-phosphate carboxylase small subunit 5B gene of *Lemna gibba* (nucleotides 689-751 of NCBI Accession No. S45167, Buzby et al. (1990) *Plant Cell* 2:805-814) and a nucleotide sequence corresponding to nucleotides 1222-1775 of the maize alcohol dehydrogenase gene (GenBank Accession Number X04049) inserted between the promoter and the polylinker. This intron sequence is shown in SEQ ID NO:1, and the leader sequence is shown in SEQ ID NO:2.

Transformation of Duckweed

Duckweed fronds or duckweed nodule cultures (derived from *Lemna minor* strain 8627 in these examples) were transformed with the expression constructs described above using *Agrobacterium*-mediated transformation methods. *Agrobacterium tumefaciens* strain C58Z707, a disarmed, broad host range C58 strain (Hepburn et al. (1985) *J. Gen. Microbiol.* 131:2961-2969) is used for transformation in these examples. The expression constructs described above were mobilized into *A. tumefaciens* by electroporation, or by a triparental mating procedure using *E. coli* MM294 harboring the mobilizing plasmid pRK2013 (Hoekema et al. (1983) *Nature* 303: 179-180; Ditta et al. (1980) *Proc. Natl. Acad. Sci. USA* 77: 7347-7350). C58Z707 strains comprising the expression constructs described above are streaked on AB minimal medium (Chilton et al., (1974) *Proc. Nat. Acad. Sci. USA* 71: 3672-3676) or in YEB or LB medium (1 g/L yeast extract, 5 g/L beef extract, 5 g/L peptone, 5 g/L sucrose, 0.5 g/L $MgSO_4$) containing streptomycin at 500 mg/L, spectinomycin at 50 mg/L and kanamycin sulfate at 50 mg/L and grown overnight at 28° C.

Duckweed nodule cultures for transformation were produced as follows. Duckweed fronds were separated, the roots are cut off with a sterile scalpel, and the fronds are placed, ventral side down, on Murashige and Skoog medium (catalog number M-5519; Sigma Chemical Corporation, St. Louis, Mo.) pH 5.6, supplemented with 5 µM 2,4-dichlorophenoxyacetic acid, 0.5 µM 1-Phenyl-3(1,2,3-thiadiazol-5-yl) urea thidiazuron (Sigma P6186), 3% sucrose, 0.4 Difco Bacto-agar (Fisher Scientific), and 0.15% Gelrite (Sigma). Fronds were grown for 5-6 weeks. At this time, the nodules (small, yellowish cell masses) appeared, generally from the central part of the ventral side. This nodule tissue was detached from the mother frond and cultured in Murashige and Skoog medium supplemented with 3% sucrose, 0.4% Difco Bacto-agar, 0.15% Gelrite, 1 µM 2,4-dichlorophenoxyacetic acid, and 2 µM benzyladenine.

Duckweed nodule cultures were transformed as follows. The appropriate *Agrobacterium tumefaciens* strain was grown on potato dextrose agar or YEB or LB agar with 50 mg/L kanamycin and 100 µM acetosyringone, and resuspended in Murashige and Skoog medium supplemented with 0.6 M Mannitol and 100 µM acetosyringone. Nodule culture tissue was inoculated by immersing in the solution of resuspended bacteria for 1-2 minutes, blotted to remove excess fluid, and plated on co-cultivation medium consisting of Murashige and Skoog medium supplemented with auxin and cytokinin optimized to promote nodule growth and 100 µM acetosyringone. See, Yamamoto et al. (2001) *In Vitro Cell Dev. Biol. Plant* 37:349-353.

For selection, nodule culture tissue was transferred to regeneration medium; 0.5 X Schenk and Hildebrandt medium supplemented with 1% sucrose 0.4% Difco Bacto-Agar, 0.15% Gelrite 500 mg/L cefotaxime, and 6 mg/L geneticin and cultured for approximately 6-8 weeks under continuous light (20-40 µM/m²·sec). The nodule tissue was transferred every 7 days to fresh culture medium. Selection is complete when the nodule tissue shows vigorous growth on the selection agent.

The following examples demonstrate the expression of biologically active plasminogen and microplasminogen in duckweed.

Example 1

Production of Plasminogen

Human plasminogen was expressed in duckweed as follows. A synthetic duckweed-codon optimized sequence encoding human plasminogen was inserted into the expression vector described above. The amino acid sequence of the encoded plasminogen is given in SEQ ID NO:4, and the duckweed-optimized coding sequence is given in SEQ ID NO:3. The expression vector also contained a duckweed optimized coding sequence encoding the rice alpha amylase signal peptide inserted 5' of the plasminogen coding sequence. The nucleotide sequence encoding the signal peptide was operably linked to the nucleotide sequence encoding human plasminogen such that the two coding sequences would be translated as one protein. The duckweed optimized coding sequence encoding the rice alpha amylase signal peptide is given in SEQ ID NO:7, and the encoded peptide is given in SEQ ID NO:8. This plasminogen expression vector is referred to as BAP01 in this example.

Duckweed lines transformed with the BAP01 expression vector were generated as described above. Due to the large size of plasminogen, the primary screening of transgenic lines included analysis of both media and tissue homogenates. The vast majority of expressed protein was retained in the tissue. A total of 81 lines were generated and plasminogen accounted for as much as 6% of the total soluble protein in plant extracts (as measured by ELISA). FIG. 1 represents the level of plasminogen measured in 56 of the transgenic lines. These levels were obtained from plants grown for 2 weeks in research vessels. Commercially available plasminogen was used as the standard in this assay.

The activity of the duckweed-expressed plasminogen was determined for tissue extracts from 7 different independent transgenic lines. The duckweed-expressed plasminogen was activated by streptokinase to produce an active complex. Activation by streptokinase does not involve the formation of plasmin, but occurs by a conformational shift that results from formation of a streptokinase/plasminogen complex. The activity of the resulting complex was then determined by assaying for cleavage of the chromogenic substrate Glu-Phe-Lys-pNA (available from Chromgenix Instrumentation Laboratory SpA, Milano Italy) shown in SEQ ID NO:9 (pNA=p-Nitroanilide) at 405 nm. (Gram J. and Jespersen J. Thromb. Haemost. 53, 255-259 (1985) and Robbins, K. C. Semin. Thromb. Haemost. 13 (2), 131-138 (1987)). For each of the seven transgenic lines tested, the activity level was closely correlated with the protein expression levels as determined by ELISA, indicating that the plasminogen produced in Lemna had a similar specific activity to that of the commercially available control protein.

It was noted that many of the duckweed lines that were engineered to over express plasminogen underwent rapid senescence. However, it was determined that senescence in these lines could be reduced by increasing the aeration and media volume during plant culture. In addition, altering the inoculum density can also influence the plant health. The culture of eight transgenic duckweed lines was scaled-up, and one of these lines, BAP01-B1-95, was selected for further analysis. This line was selected based on biomass accumulation, plasminogen expression level (3.3% of total soluble protein levels in crude plant extracts as determined by ELISA), and overall plant health.

Plasminogen was harvested from the BAP01-B1-95 line as follows. Bulk duckweed tissue was homogenized, clarified by centrifugation, filtered through a 0.22 µM filter, passed through a Dowex ion exchange resin column (available from Dow Chemical, Midland, Mich.), and then affinity purified by lysine Sepharose chromatography. Bound material was eluted from the affinity column with ε-amino caproic acid. Crude tissue extracts obtained from these plants contained plasminogen as 3.3% of the total soluble protein as measured by ELISA.

Figure 2:
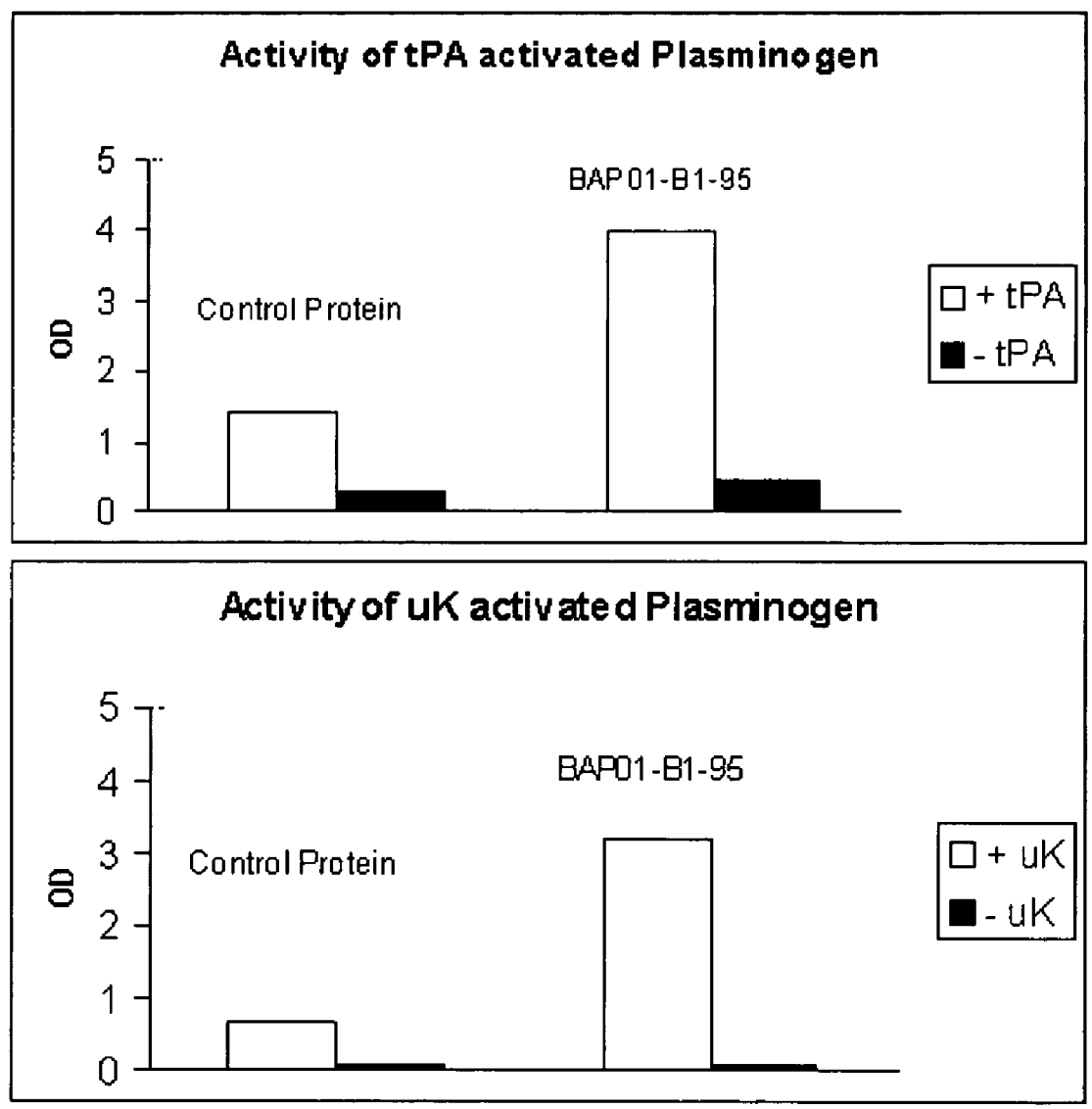
FIG. 2 shows the activity of plasmin produced by activating duckweed-produced plasminogen with tPA. See Example 1 in the Experimental section for additional details.
Figure 3:
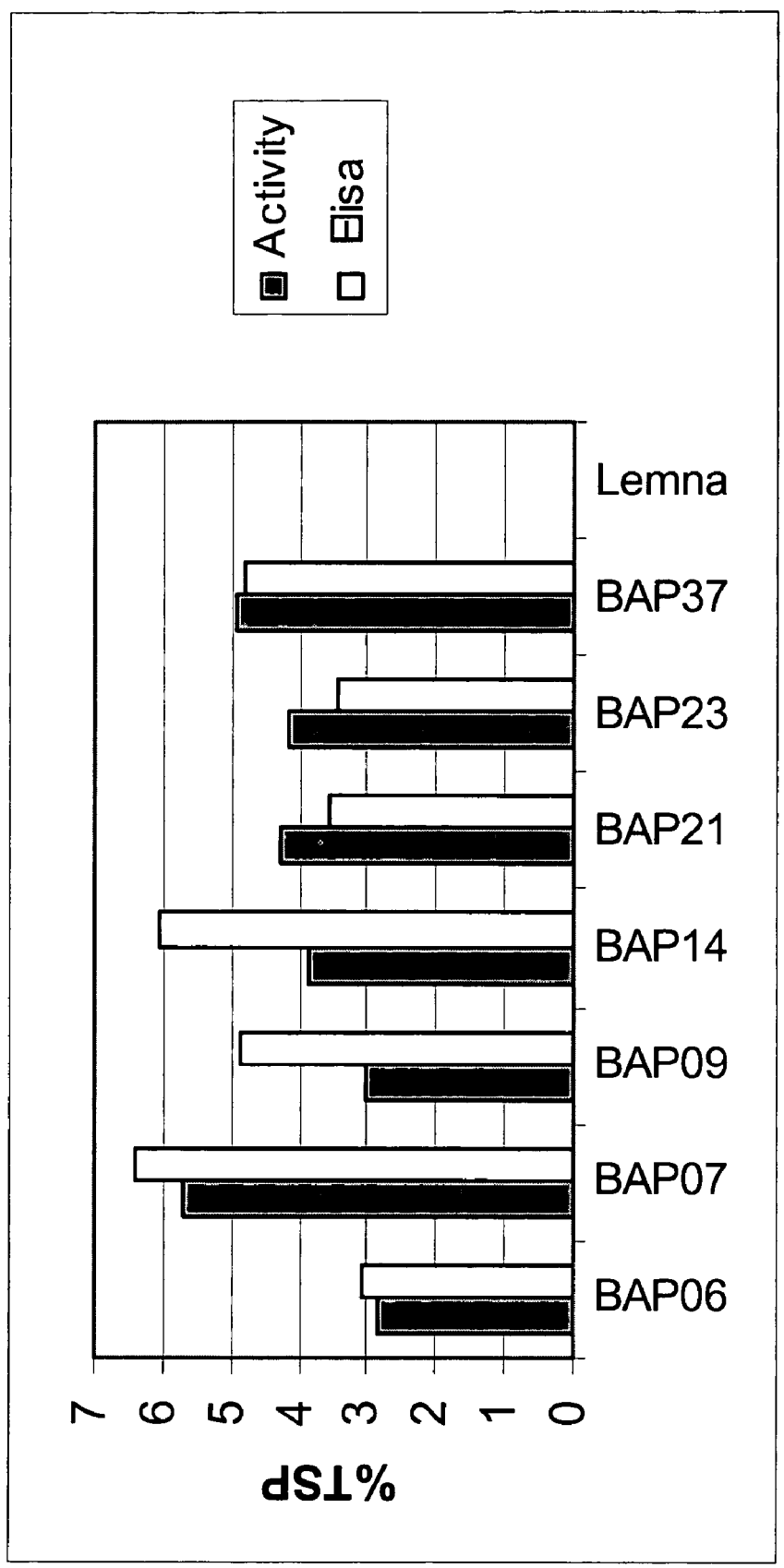
FIG. 3 shows the quantitation of plasminogen by ELISA compared to plasmin activity after streptokinase activation. For the lines tested, quantitation by ELISA and streptokinase activity assay gave comparable values, indicating that Lemna-produced plasminogen has a similar specific activity to the control protein. See Example 1 in the Experimental section for additional details.
Figure 6:
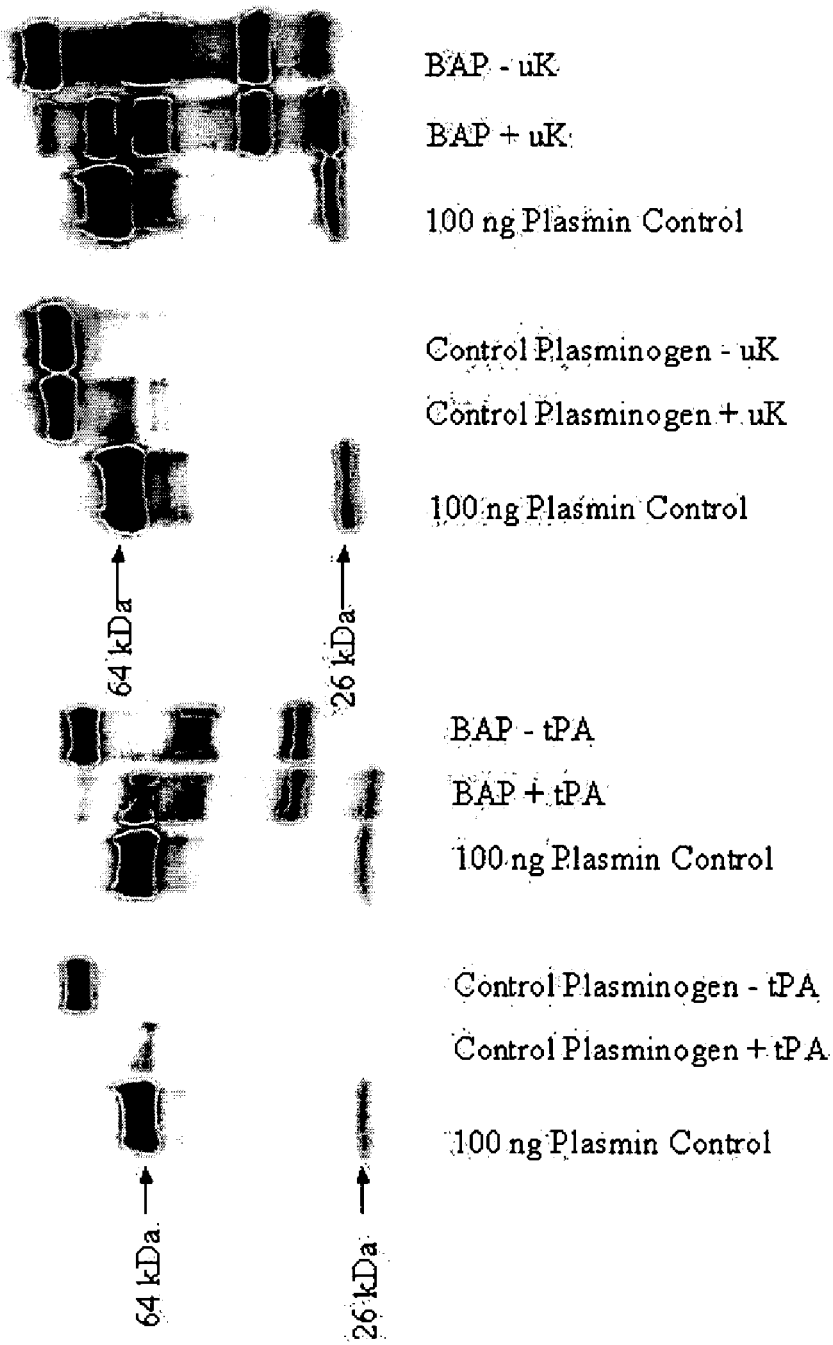
FIG. 6 shows the formation of plasmin after urokinase or tPA activation of Lemna-produced plasminogen. "BAP" designates the Lemna-produced plasminogen. The left panel shows activation with tissue plasminogen activator (tPA) and the right panel shows activation with urokinase (uK). See Example 1 in the Experimental section for additional details.

The activity of the duckweed-produced plasminogen following activation by tPA urokinase, and streptokinase was also determined. Activity of plasminogen activated with either tPA or urokinase produced activated plasmin as shown in FIG. 2. Western blotting analysis showed that both the heavy and light chain of the plasmin produced by activation the duckweed-produced plasminogen co-migrated with the commercially available plasmin used as a control (FIG. 6). Activation with streptokinase also produced activated plasminogen as shown in SEQ ID NO:3. In this assay, plasminogen is activated by streptokinase to produce an active complex, which then cleaves a chromogenic substrate (Coamatic® brand plasminogen kit, DiaPharma, West Chester, Ohio). FIG. 3 shows that for the lines tested, quantitation by ELISA and streptokinase activity assay gave comparable values, indicating that Lemna-produced plasminogen has a similar specific activity to the control protein.

The size of the duckweed-produced plasminogen was determined by Western blotting using an anti-plasminogen antibody available from American Diagnostica, Inc. Greenwich, Conn. This analysis showed that 60% of the plasminogen produced in duckweed was full length N-terminal sequencing of the duckweed produced plasminogen showed further processing producing a polypeptide missing the first 74 amino acids. In human serum, plasminogen is isolated as a mixture of unprocessed 'glu-plasminogen' and several processed versions defined as 'lys-plasminogen' where 69, 77, or 78 N-terminal amino acids are removed. Such a cleavage has no effect on activity.

Figure 4:
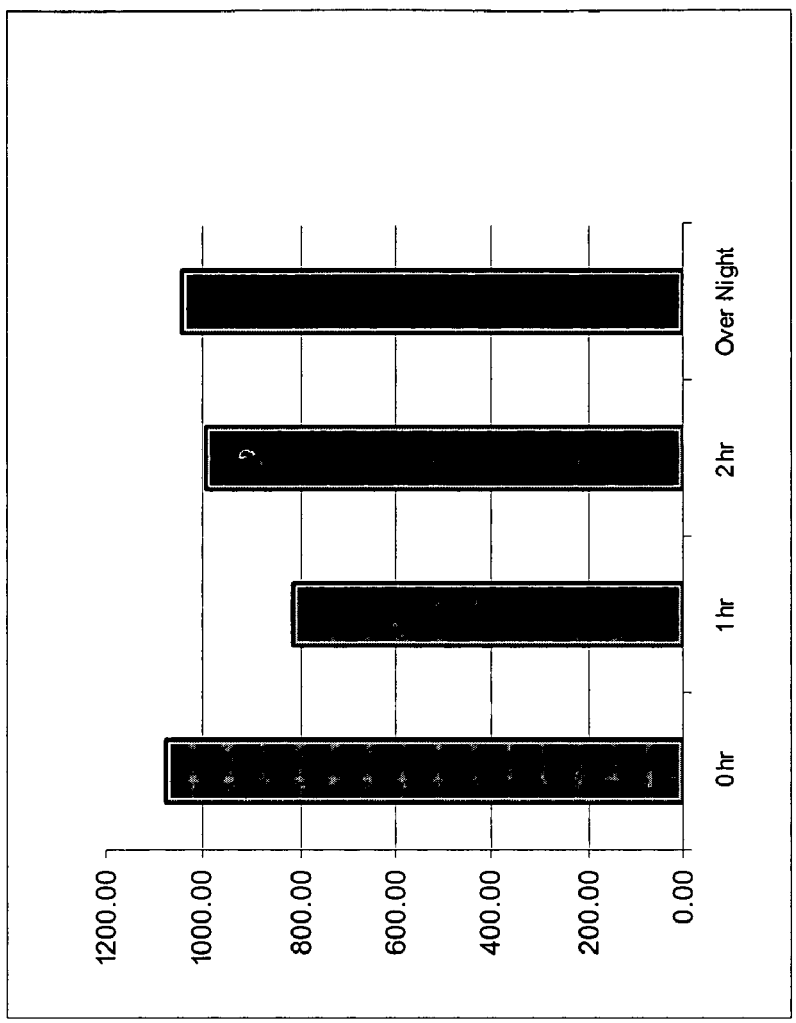
FIG. 4 shows the stability of human plasminogen spiked into Lemna tissue extract. See Example 1 in the Experimental section for additional details.
Figure 4:
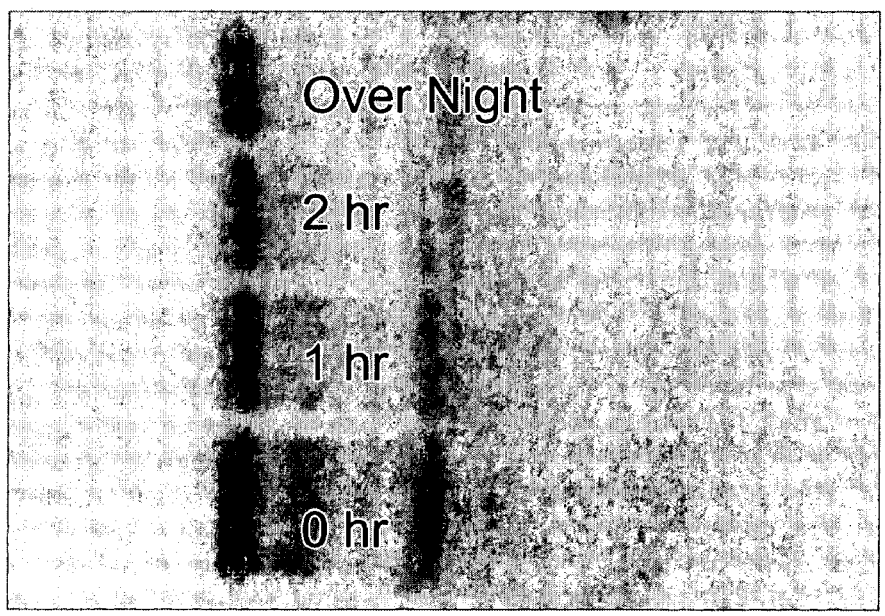
Figure 5:
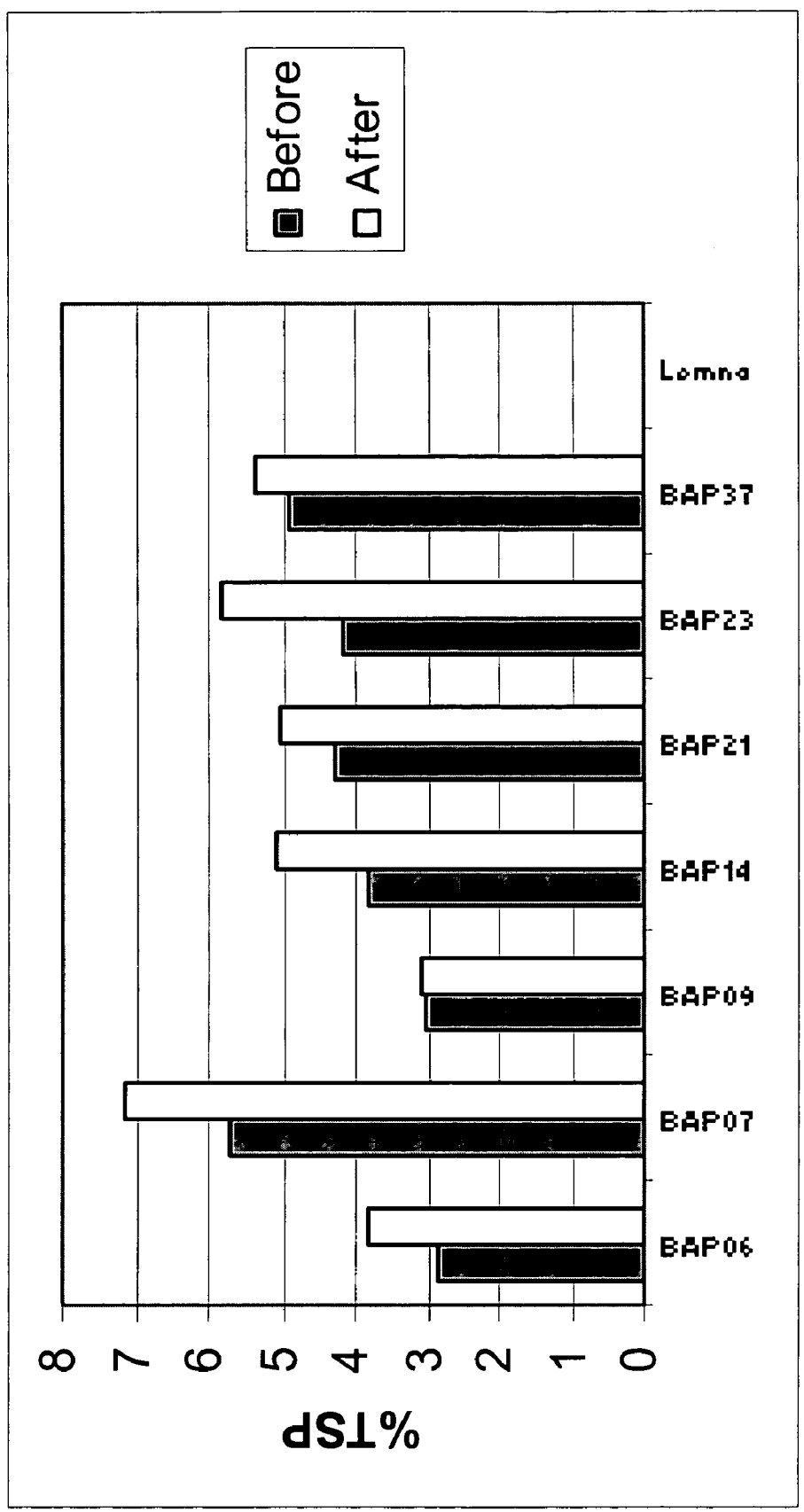
FIG. 5 shows the stability of Lemna plasminogen in tissue extract after freeze/thaw as measured by an activity assay. See Example 1 in the Experimental section for additional details.

Because references in the prior art have reported difficulty in producing stable plasminogen in recombinant systems, the stability of plasminogen produced in the Lemna system was tested. FIG. 4 demonstrates the stability of human plasminogen added to a Lemna tissue extract. The figure demonstrates that the human plasminogen retained almost all of its activity even after an overnight incubation in the Lemna extract. FIG. 5 demonstrates the stability of Lemna-produced plasminogen in Lemna tissue extracts following a freeze-thaw cycle. The figure demonstrates that the Lemna-produced protein is stable following a freeze-thaw cycle.

Example 2

Production of Microplasminogen in Duckweed

Human microplasminogen was expressed in duckweed as follows. A synthetic duckweed-codon optimized sequence encoding human microplasminogen was inserted into the expression vector described above. The amino acid sequence of the encoded microplasminogen is given in SEQ ID NO:6, and the duckweed-optimized coding sequence is given in SEQ ID NO:5. The expression vector also contained a duckweed optimized coding sequence encoding the rice alpha amylase signal peptide inserted 5' of the plasminogen coding sequence. The nucleotide sequence encoding the signal peptide was operably linked to the nucleotide sequence encoding human microplasminogen such that the two coding sequences would be translated as one protein. The duckweed optimized coding sequence encoding the rice alpha amylase signal peptide is given in SEQ ID NO:7, and the encoded peptide is given in SEQ ID NO:8. This microplasminogen expression vector is referred to as BAMP01 in this example.

Figure 7:
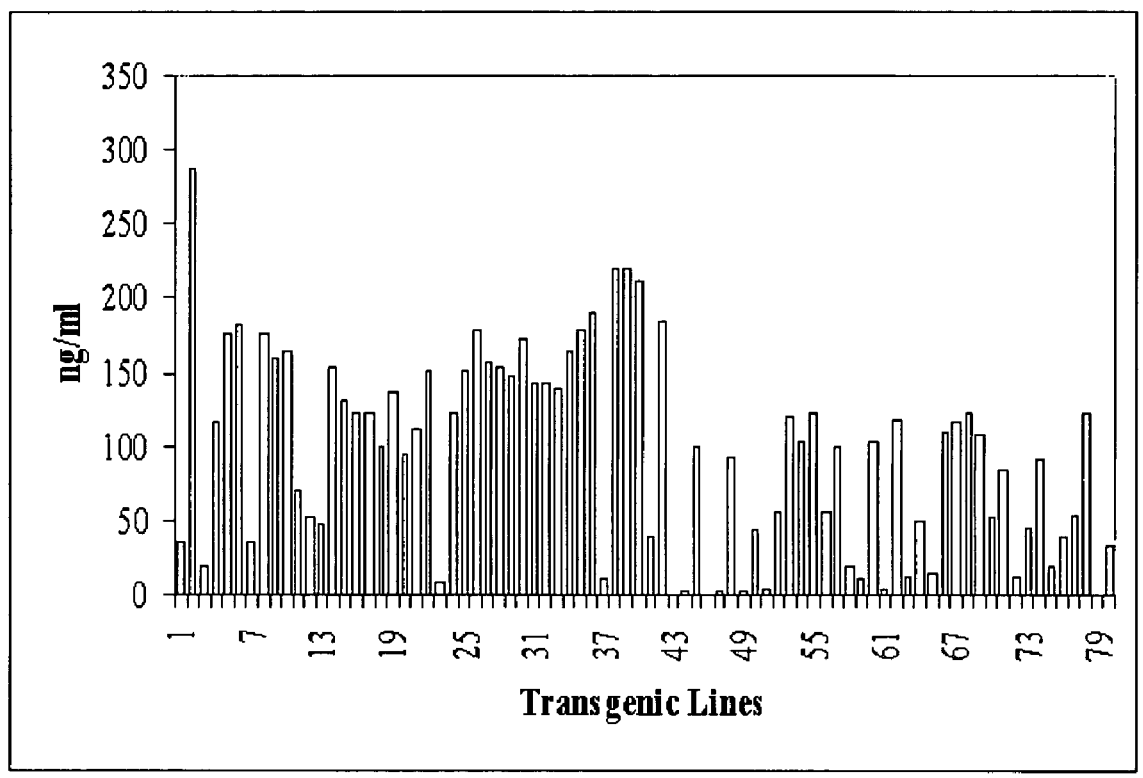
FIG. 7 shows the concentration of microplasminogen as measured by ELISA in media from 79 duckweed lines that were transformed with the microplasminogen expression construct BAMP01. See Example 2 in the Experimental section for additional details.

Duckweed lines transformed with the BAMP01 expression vector were generated as described above. The majority of the expressed microplasminogen was secreted into the culture medium. 79 transgenic lines were screened to determine microplasminogen expression levels. FIG. 7 shows the levels of microplasminogen expressed in these lines. The first set of 42 lines were grown for 7 days, while the second set of 37 lines were grown for six days. It should be noted that duckweed is unique in that it grows in very dilute aqueous media inorganic media with a very low protein content, distinguishing it from type fermentation based systems and mammalian cell-based expression systems. The duckweed growth media typically contains only 30 mg/L of host plant proteins. This low level of host plant protein provides advantages for the downstream purification of the secreted protein.

One of the BAMP01 transformed duckweed lines, BAMP01-B1-58, was selected for further study. Microplasminogen was harvested from the culture media of the BAMP01-B1-58 line as follows. The culture media was process by ultrafiltration and diafiltration and then passed over a Dowex ion exchange resin column (available from Dow Chemical, Midland, Mich.) to remove low molecular weight plant metabolites. The concentration before concentrating of microplasminogen in the crude aqueous media was approximately 20 mg/L as determined by quantitative Western blotting.

The size of the duckweed-produced microplasminogen was determined by Western blotting using an anti plasminogen antibody available from (American Diagnostica Inc. Greenwich, Conn.). This analysis showed that most of the microplasminogen produced in duckweed was full length. An intact N-terminus was confirmed also by N-terminal sequencing The activity of the duckweed-expressed microplasminogen was determined for the BAMP01-B1-58 transgenic line following activation by streptokinase to produce an active complex as described above for plasminogen. The duckweed-produced microplasminogen showed some level of activity in the absence of streptokinase, and a significant increase in activity following activation by streptokinase.

Like plasminogen, microplasminogen can be activated by urokinase and tPA; however, only the B-chain is produced. Western blot analysis confirmed the production of the B chain of plasmin following activation of duckweed-produced microplasminogen with either urokinase or tPA.

Figure 8:
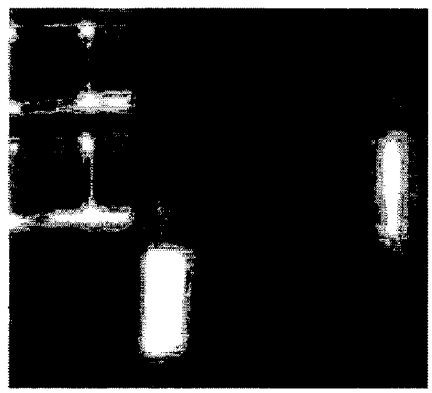
FIG. 8 shows a zymogram analysis of Lemna-produced microplasminogen after activation by tPA. The figure shows the presence of an active proteolytic band that is not present in concentrated control media. See Example 2 in the Experimental section for additional details.

To confirm the activity of plasmin from *Lemna*-produced microplasminogen a gelatin zymogram was run on concentrated media following activation by tPA. FIG. 8 shows the presence of an active proteolytic band that is not present in concentrated control media.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

What is claimed is:

1. A method for producing high levels of stable plasminogen in duckweed, wherein said method comprises the steps of:
   (a) culturing a duckweed plant or duckweed plant cell or nodule, wherein said duckweed plant or duckweed plant cell or nodule is stably transformed with a nucleic acid molecule comprising a nucleotide sequence encoding plasminogen, wherein said nucleic acid molecule comprises:
   1) duckweed-preferred codons in the coding sequence for said plasminogen;
   2) an operably linked nucleotide sequence comprising a plant intron that is inserted upstream of the coding sequence for said plasminogen;
   3) an operably linked nucleotide sequence coding for a signal peptide, said signal peptide-encoding sequence inserted between said intron and said plasminogen-encoding sequence; and
   4) an operably linked nucleotide sequence comprising the translation leader sequence from the ribulose-bis-phosphate carboxylase small subunit 5B gene of *Lemna gibba*; and
   (b) collecting said stable plasminogen from said duckweed plant or duckweed plant cell or nodule.

2. The method according to claim 1, wherein the nucleotide sequence encoding plasminogen comprises between 70-100% duckweed-preferred codons.

3. The method according to claim 1, wherein said plant intron is an intron from maize alcohol dehydrogenase 1 gene.

4. The method according to claim 3, wherein said plant intron is SEQ ID NO: 1.

5. The method according to claim 1, wherein said translation leader sequence is SEQ ID NO:2.

6. The method according to claim 1, wherein said plasminogen is human plasminogen.

7. The method according to claim 6, wherein said plasminogen has at least 95% sequence identity with SEQ ID NO:4.

8. The method according to claim 1, wherein at least 2% of soluble protein in the duckweed plant or duckweed plant cell or nodule is stable plasminogen.

9. The method according to claim 8, wherein at least 3% of soluble protein in the duckweed plant or duckweed plant cell or nodule is stable plasminogen.

10. The method according to claim 9, wherein at least 4% of soluble protein in the duckweed plant or duckweed plant cell or nodule is stable plasminogen.

11. A method for producing high levels of stable plasminogen in duckweed, wherein the method comprises the steps of:
    (a) culturing a duckweed plant or duckweed plant cell or nodule, wherein the duckweed plant or duckweed plant cell or nodule is stably transformed with a nucleic acid molecule comprising a nucleotide sequence encoding plasminogen, wherein the nucleotide sequence is SEQ ID NO:3; and
    (b) collecting stable plasminogen from the duckweed plant or duckweed plant cell or nodule.

12. The method of claim 11, wherein said nucleic acid molecule comprises at least one attribute selected from the group consisting of:
    (a) an operably linked nucleotide sequence comprising a plant intron that is inserted upstream of the nucleotide sequence encoding plasminogen; and
    (b) an operably linked nucleotide sequence comprising a translation leader sequence.

13. A method for producing high levels of stable plasminogen in duckweed, wherein said method comprises the steps of:
    (a) culturing a duckweed plant or duckweed plant cell or nodule, wherein said duckweed plant or duckweed plant cell or nodule is stably transformed with a nucleic acid molecule comprising a nucleotide sequence encoding plasminogen, said plasminogen having at least 95% sequence identity with SEQ ID NO:4, wherein said nucleic acid molecule comprises:
    1) duckweed-preferred codons in the coding sequence for said plasminogen;
    2) an operably linked nucleotide sequence comprising a plant intron that is inserted upstream of the coding sequence for said plasminogen, wherein said plant intron is SEQ ID NO:1; and
    3) an operably linked nucleotide sequence comprising a translation leader sequence, wherein said translation leader sequence is SEQ ID NO:2; and
    (b) collecting said stable plasminogen from said duckweed plant or duckweed plant cell or nodule.

14. The method according to claim 1, wherein said signal peptide is a rice alpha-amylase signal peptide.

15. The method according to claim 14, wherein said signal peptide comprises SEQ ID NO:8.

16. The method according to claim 15, wherein said signal peptide is encoded by a nucleotide sequence comprising SEQ ID NO:7.

* * * * *